(12) United States Patent
Yu et al.

(10) Patent No.: US 10,653,603 B2
(45) Date of Patent: *May 19, 2020

(54) N-ACYLDIPEPTIDE DERIVATIVES AND THEIR USES

(71) Applicant: NeoStrata Company, Inc., Princeton, NJ (US)

(72) Inventors: Ruey J. Yu, Chalfont, PA (US); Eugene J. Van Scott, Abington, PA (US)

(73) Assignee: NEOSTRATA COMPANY, INC., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,474

(22) Filed: Jan. 17, 2017

(65) Prior Publication Data

US 2017/0119646 A1    May 4, 2017

Related U.S. Application Data

(60) Continuation of application No. 15/171,601, filed on Jun. 2, 2016, which is a continuation of application No. 14/718,317, filed on May 21, 2015, now Pat. No. 9,370,546, which is a division of application No. 14/354,711, filed as application No. PCT/US2012/062715 on Oct. 31, 2012, now Pat. No. 9,067,969.

(60) Provisional application No. 61/582,675, filed on Jan. 3, 2012, provisional application No. 61/554,724, filed on Nov. 2, 2011, provisional application No. 61/552,751, filed on Oct. 28, 2011.

(51) Int. Cl.

| | |
|---|---|
| *A61K 8/64* | (2006.01) |
| *C07K 5/02* | (2006.01) |
| *C07K 5/062* | (2006.01) |
| *C07K 5/078* | (2006.01) |
| *C07K 5/072* | (2006.01) |
| *A61K 31/07* | (2006.01) |
| *A61K 8/67* | (2006.01) |
| *A61K 38/05* | (2006.01) |
| *A61Q 19/00* | (2006.01) |
| *A61Q 19/08* | (2006.01) |
| *C07K 5/065* | (2006.01) |
| *C07K 5/06* | (2006.01) |
| *A61K 9/00* | (2006.01) |
| *A61Q 19/06* | (2006.01) |
| *A61Q 5/00* | (2006.01) |
| *A61Q 19/02* | (2006.01) |

(52) U.S. Cl.
CPC .............. *A61K 8/64* (2013.01); *A61K 8/671* (2013.01); *A61K 9/0014* (2013.01); *A61K 31/07* (2013.01); *A61K 38/05* (2013.01); *A61Q 19/00* (2013.01); *A61Q 19/06* (2013.01); *A61Q 19/08* (2013.01); *C07K 5/0202* (2013.01); *C07K 5/0205* (2013.01); *C07K 5/0207* (2013.01); *C07K 5/0606* (2013.01); *C07K 5/06026* (2013.01); *C07K 5/06034* (2013.01); *C07K 5/06043* (2013.01); *C07K 5/06052* (2013.01); *C07K 5/06069* (2013.01); *C07K 5/06078* (2013.01); *C07K 5/06113* (2013.01); *C07K 5/06147* (2013.01); *C07K 5/06156* (2013.01); *C07K 5/06165* (2013.01); *C07K 5/06191* (2013.01); *A61K 2800/10* (2013.01); *A61K 2800/92* (2013.01); *A61Q 5/00* (2013.01); *A61Q 19/007* (2013.01); *A61Q 19/008* (2013.01); *A61Q 19/02* (2013.01); *Y02A 50/463* (2018.01)

(58) Field of Classification Search
CPC ........................................................ A61K 8/64
See application file for complete search history.

(56) References Cited

U.S. PATENT DOCUMENTS

| | | | |
|---|---|---|---|
| 5,002,760 | A | 3/1991 | Katzev |
| 5,534,538 | A | 7/1996 | Drauz et al. |
| 5,607,921 | A | 3/1997 | Bernard et al. |
| 5,837,218 | A | 11/1998 | Peers et al. |
| 6,159,485 | A | 12/2000 | Yu et al. |
| 6,524,593 | B1 | 2/2003 | Yu et al. |
| 6,620,419 | B1 | 9/2003 | Lintner |
| 6,852,699 | B1 | 2/2005 | Schonrock et al. |
| 7,326,326 | B2 | 2/2008 | Chang et al. |
| 7,807,625 | B2 | 10/2010 | Majewski et al. |
| 9,067,969 | B2 | 6/2015 | Yu et al. |

(Continued)

FOREIGN PATENT DOCUMENTS

| | | |
|---|---|---|
| EP | 2771020 A2 | 9/2014 |
| FR | 2776188 A1 | 9/1999 |

(Continued)

OTHER PUBLICATIONS

Ichihashi et al. "Photoaging of the skin," Anti-Aging Medicine, 2009, 6(6): 46-59 (Year: 2009).*

(Continued)

*Primary Examiner* — Christina Bradley
(74) *Attorney, Agent, or Firm* — Ice Miller LLP

(57) ABSTRACT

Methods of treating aging related skin changes and of increasing skin thickness with topical administration of N-acyldipeptide derivatives are described. Compositions comprising N-acyldipeptide derivatives, are therapeutically effective for increasing skin thickness, and for treating extrinsic and intrinsic aging and aging related skin changes, such as fine lines, wrinkles, photoaging, hyperpigmentation, laxity, age spots, lentigines, mottled skin, and cellulite.

21 Claims, No Drawings

(56) References Cited

U.S. PATENT DOCUMENTS

| | | | |
|---|---|---|---|
| 9,370,546 | B2 | 6/2016 | Yu et al. |
| 2003/0194445 | A1 | 10/2003 | Kuhner et al. |
| 2005/0080011 | A1 | 4/2005 | Somers et al. |
| 2007/0128265 | A1 | 6/2007 | Holick |
| 2007/0231284 | A1 | 10/2007 | Pinel et al. |
| 2010/0022459 | A1 | 1/2010 | Gazit |
| 2010/0304363 | A1 | 12/2010 | Lee et al. |
| 2011/0183914 | A1 | 7/2011 | Osborne |
| 2011/0206752 | A1 | 8/2011 | Carreno Serraima et al. |
| 2012/0070392 | A1 | 3/2012 | Lee et al. |
| 2012/0183555 | A1 | 7/2012 | Chang et al. |

FOREIGN PATENT DOCUMENTS

| | | | |
|---|---|---|---|
| FR | 2894144 | A1 | 6/2007 |
| JP | H05-170636 | A | 7/1993 |
| WO | 2007143006 | A2 | 12/2007 |
| WO | 2009049172 | A1 | 4/2009 |
| WO | 2009148947 | A1 | 12/2009 |
| WO | 2010065342 | A1 | 6/2010 |
| WO | 2010114275 | A2 | 10/2010 |
| WO | 2011048390 | A2 | 4/2011 |
| WO | 2013063615 | A2 | 5/2013 |

OTHER PUBLICATIONS

Obagi ("Why does skin wrinkle with age? What is the best way to slow or prevent this process?" Scientific American, Sep. 26, 2005) (Year: 2005).*

Partial Search Report dated Sep. 12, 2017 in EP Application No. 17180167.3.

Dalal et al. "Multiple Myeloma Unveiled by Multiple Hyperkeratotic Spicules"; Isr. Med. Assoc. J.; Nov. 2010 (Nov. 2010) vol. 12, No. 11; pp. 709-710; p. 709, para 1-2.

Livant et al, "Anti-invasive, antitumorigenic, and antimetastatic activities of the PHSCN sequence in prostate carcinoma," Cancer Research, vol. 60, No. 2, pp. 309-320 (Jan. 15, 2000).

Lambert, "The nociceptin/orphanin FQ receptor: a target with broad therapeutic potential," Nature Reviews Drug Discovery, vol. 7, No. 8, pp. 694-710 (Aug. 1, 2008).

Gottschalck et al, "International Cosmetic Ingredient Dictionary and Handbook," The Costmetic, Toiletry, and Fragrance Association, Washington, p. 2712 (2006).

Sorg et al, "Stufenweise Synthese von Oligotryosinpeptiden," Liebigs Ann. Chem., vol. 734, pp. 180-186 (Jan. 1, 1970).

Sandhu et al, "Peptide binding specificity of the chaperon calreticulin," Biochimica et Biophysica Acta (BBA)—Proteins & Proteomics, vol. 1774, No. 6, pp. 701-713 (Jun. 5, 2007).

Fitzen et al, "Peptide-binding specificity of the prosurfactant protein C Brichos domain analyzed by electrospray ionization mass spectrometry," Rapid Communications in Mass Spectrometry, vol. 23, No. 22, pp. 3591-3598 (Nov. 1, 2009).

Woithe et al, "Exploring the substrate specificity of OxyB, a phenol coupling P450 enzyme involved in vancomycin biosynthesis," Organic & Biomolecular Chemistry, vol. 6, No. 16, pp. 2861-2867 (Aug. 1, 2008).

Oja et al, "Amino Acids and Peptides in the Nervous System," Handbook of Neurochemistry and Molecular Neurobiology 3rd Ed., Springer Science, pp. 401-411 (2007).

Sabherwal et al., "Integrin alpha2beta1 Mediates the Anti-Angiogenic and Anti-Tumor Activities of Angiocidin, a Novel Tumor-Associated Protein," Experimental Cell Research, vol. 312, pp. 2443-2453 (2006).

Tuszynski et al., "G-protein coupled receptor-associated sorting protein 1 (GASP-1), a potential biomarker in breast cancer," Experimental and Molecular Pathology, vol. 91, pp. 608-613 (2011).

Zhou et al., "Cloning and Characterization of Angiocidin, a Tumor Cell Binding Protein for Thrombospondin-1," J. Cellular Biochemistry, vol. 92, pp. 125-146 (2004).

Alfonso et al, "Diagnosis, treatment and follow-up of the carpal tunnel syndrome: a review," Neurol. Sci., vol. 31, pp. 243-252 (2010).

Singh et al, "Herpes Zoster: A Clinical Review," J. Infect. Dis. Anti. Microb. Agent, vol. 23, No. 3, pp. 211-222 (2010).

Huse et al, "Targeting brain cancer: advances in the molecular pathology of malignant glioma and medulloblastoma," Nature Reviews—Cancer, vol. 10, pp. 319-331 (2010).

Zolopa, "The evolution of HIV treatment guidelines: Current state-of-the-art of ART," Antiviral Research, vol. 85, pp. 241-244 (2010).

American Diabetes Association, "Standards of Medical Care in Diabetes—2010," Diabetes Care, vol. 33, No. 1 pp. S11-S61 (2010).

Rekharsky et al, "Complexation and Chiral Recognition Thermodynamics of [gamme]-Cyclodextrin with N-Acetyl-and N-Carbobenzyloxy-dipeptides Possessing Two Aromatic Rings," The Journal of Organic Chemistry, vol. 68., No. 13, pp. 5228-5235 (Jun. 2003).

Hagermark et al., "Potentiation of Itch and Flare Responses in Human Skin by Prostaglandins E2 and H2 and a Prostaglandin Endoperoxide Analog," Journal of Investigative Dermatology, vol. 69, No. 6, pp. 527-530 (1977).

Akamatsu et al., "Quantitative Analyses of the Structure-Hydrophobicity Relationship for N-Acetyl Di- and Tripeptide Amides," Journal of Pharmaceutical Sciences, vol. 83, No. 7, pp. 1026-1033 (1994).

Rella et al., "Oxidation of Peptides by Methyl(trifluoromethyl)dioxirane: The Protecting Group Matters," J. Org. Chem., vol. 72, No. 2, pp. 525-531 (2007).

Tan et al, "Design, Synthesis, and Characterization of Peptide-Based Rab Geranylgerany Transferase Inhibitors", Journ. of Med. Chemistry, vol. 52, No. 24, pp. 8025-8037, (Dec. 24, 2009).

Krattiger et al, "Water-Soluble Diketopiperazine Receptors—Selctive Recognition of Arginine-Rich Peptides", SYNLETT, No. 4, pp. 706-708, (Jan. 1, 2005).

Huang et al., "Biomimetic Peptoid Oligomers as Dual-Action Antifreeze Agents", Proceed. of the National Academy of Sciences, vol. 109, No. 49, pp. 19922-19927, (Nov. 19, 2012).

Ringseis et al., "Tripeptides from Dietary Proteins Inhibit TNFalpha-Induced Monocyte Adhesion to Human Aortic Endothelial Cells", Reg. Peptides, Elsevier Science, vol. 154, No. 1-3, pp. 91-96, (Apr. 10, 2009).

Sinaga et al., "Increasing Paracellular Porosity by E-Cadherin Peptides: Discovery of Bulge and Groove Regions in be EC1-Domain of E-Cadherin", Pharm. Research, vol. 19, No. 8, pp. 1170-1179, (Aug. 1, 2002).

Chen et al., "Synthesis and Biological Activity of Some Val(Ala)-Tyr and Val-Tyr-Tyr Peptides", ACTA Pharma, vol. 27, No. 12, pp. 895-902, (Jan. 1, 1992).

Hui et al., "Chemical Partitioning into Powdered Human Stratum Corneum", Dermatotoxicology: A Useful in Vitro Model for Studying Interaction of Chemical and Human Skin, Chapter 7, pp. 106-121 (2004).

Mayo Clinic, Numbeness, downloaded from webpage: http://www.mayoclinic.org/symptoms/numbness/basics/causes/sym-20050938; download date: Jul. 11, 2016, Original Posting date: Apr. 8, 2016.

Mayo Clinic, Joint Pain, downloaded from webpage: http://www.mayoclinic.org/symptoms/joint-pain/basics/causes/sym-20050668; download date: Jul. 11, 2016, Original Posting date: Feb. 26, 2016.

Mayo Clinic, Arthritis Symptoms, downloaded from webpage: http://www.mayoclinic.org/diseases-conditions/arthritis/symptoms-causes/dxc-20168905 download date: Jul. 11, 2016, Original Posting date: Jan. 7, 2016.

Mayo Clinic, Arthritis Treatment, downloaded from webpage: http://www.mayoclinic.org/diseases-conditions/arthritis/diagnosis-treatment/treatment/txc-20169117: download date: Jul. 11, 2016, Original Posting date: Jan. 7, 2016.

Mayo Clinic, Sunburn, downloaded from webpage: http://www.mayoclinic.org/diseases-conditions/sunburn/basics/definition/con-20031065: download date: Jul. 11, 2016, Original Posting date: May 1, 2014.

Int'l Search Report and Written Opinion dated Mar. 5, 2013 in Int'l Application No. PCT/US2012/062715.

(56) References Cited

OTHER PUBLICATIONS

Thermo Electron Corporation, "N-Terminal Acetylation and C-Terminal Amidation of Peptides," Thermo Electron GmbH (2004).
Beers et al., "Skin Growths: Bumps and Spots," The Merck Manual of Health and Aging, pp. 496 (2005).
Int'l Preliminary Report on Patentability dated Oct. 1, 2014 in Int'l Application No. PCT/US2012/062715.

* cited by examiner

N-ACYLDIPEPTIDE DERIVATIVES AND THEIR USES

CROSS-REFERENCE TO RELATED APPLICATIONS

This application is a continuation of U.S. patent application Ser. No. 15/171,601, filed Jun. 2, 2016, which is a continuation of U.S. patent application Ser. No. 14/718,317, filed May 21, 2015, now U.S. Pat. No. 9,370,546, issued Jun. 21, 2016, which is a divisional of U.S. patent application Ser. No. 14/354,711 filed Apr. 28, 2014, now U.S. Pat. No. 9,067,969, issued Jun. 30, 2015, which is a Section 371 of International Application No. PCT/US2012/062715, filed Oct. 31, 2012, which was published on May 2, 2013, under International Publication No. WO 2013/063615 A2, which claims priority under 35 U.S.C. § 119(e) to Provisional Patent Application No. 61/552,751, filed on Oct. 28, 2011, Provisional Patent Application No. 61/554,724, filed on Nov. 2, 2011, and Provisional Patent Application No. 61/582,675, filed on Jan. 3, 2012, and the disclosures of which are incorporated by reference herein in their entireties.

FIELD OF THE INVENTION

The embodiments described herein relate to compositions and uses of the compositions comprising N-acyldipeptide derivatives for systemic or topical administration to a mammal to alleviate or improve diseases, symptoms or syndromes associated with tumors, cancers, immune, nervous, vascular, musculoskeletal or cutaneous system, or other tissues and systems.

BACKGROUND OF THE INVENTION

It was reported that a peptide ester, Asp-Phe-OMe (Aspartame), had sucrose-like sweet taste, but all other related peptides such as Ala-Phe-OMe, His-Phe-OMe, etc. had bitter taste. See Mazur et al. "Structure-Taste Relationships of Some Small Peptides" in PEPTIDES: Chemistry and Biochemistry by Boris Weinstein and Saul Lande (Marcel Dekker, Inc. New York), 1970, 175-180. In Handbook of Neurochemistry and Molecular Neurobiology $3^{rd}$ Ed. "Amino Acids and Peptides in the Nervous System" by Oja et al. Springer Science 2007, page 401-411, Reichelt describes in "Low Molecular Weight Peptides" endogenous peptides. The endogenous dipeptide described is N-pyroglutamyl (N-PyroE) peptide, N-PyroE-His-Pro-$NH_2$. In Enzyme and Microbial Technology 45 (2009) 457-462, entitled "Availability of tyrosine amide for α-chymotrypsin-catalyzed synthesis of oligo-tyrosine peptides" Narai-Kanayama et al. describe that oligo-tyrosine peptides such as Tyr-Tyr having angiotensin I-converting enzyme inhibitory activity can be synthesized by an α-chymotrypsin-catalyzed reaction with N—Ac-Tyr-OEt and Tyr-OEt or Tyr-$NH_2$ as starting substances. Kinetic analysis showed that assumed products, N—Ac-Tyr-Tyr-OEt or N—Ac-Tyr-Tyr-$NH_2$ did not hydrolyze to yield the desired Tyr-Tyr. There is no description or report about the composition or use of the composition comprising N-acyldipeptide derivatives of the present invention.

BRIEF SUMMARY OF THE INVENTION

It has been discovered in the present invention that compositions comprising the N-acyldipeptide derivatives are therapeutically effective for topical or systemic administration to alleviate or improve conditions, disorders, diseases, symptoms or syndromes associated with tumors, cancers, immune, nervous, vascular, musculoskeletal or cutaneous system, or other tissues or systems in a subject.

According to one embodiment of the present invention, the N-acyldipeptide derivative is represented by the following generic Formula (I):

$$R_1\text{-AAB-AAC-}R_2 \qquad \text{Formula (I)}$$

or an isomer, free acid, base, salt, lactone, amide, hydrazide, or ester thereof,
wherein $R_1$ is an acyl radical having up to 19 carbon atoms; AAB is an amino terminal amino acid residue selected from any amino acid; AAC is a carboxyl terminal amino acid residue selected from any amino acid; $R_2$ is $OR_3$, $NHR_4$ or $NHNHR_5$; $R_3$ is H, an alkyl, aralkyl or aryl radical having up to 19 carbon atoms; $R_4$ or $R_5$ is independently H, OH, an alkyl, aralkyl, aryl or acyl radical having up to 19 carbon atoms; a side chain of each of AAB and AAC optionally and independently has an extra functional radical selected from the group consisting of OH, SH, $NHCONH_2$, NHC(=NH)$NH_2$, $NH_2$, COOH, $CONH_2$, imidazolyl, pyrrolidinyl and indolyl; and the H or OH of the extra functional radical is optionally substituted by $NH_2$, an acyl, alkyl, aralkyl, or aryl radical having up to 19 carbon atoms.

In a preferred embodiment, AAB is an amino terminal amino acid residue selected from the group consisting of Ala, βAla, Abz, Asn, Cre, Cys, Dopa, Gly, Gln, Glu Gaba, His, Hpg, Ile, Leu, Pgly, Phe, Pro, Ser, Trp, Tyr, and Val; and AAC is a carboxyl terminal amino acid residue selected from the group consisting of Ala, Cre, Cys, Dopa, Gly, His, Hpg, Ile, Leu, Lys, Pgly, Phe, Pro, Trp and Tyr.

In another aspect, an embodiment of the present invention relates to a composition comprising a therapeutically effective amount of an N-acyldipeptide derivative of the invention and a pharmaceutically or cosmetically acceptable carrier for topical or systemic administration to a subject.

In yet another aspect, an embodiment of the present invention relates to a method of alleviating or improving conditions, disorders, diseases, symptoms or syndromes associated with tumors, cancers, immune, nervous, vascular, musculoskeletal or cutaneous system, or other tissues or systems in a subject. The method comprises topically or systemically administering to the subject a composition of the present invention.

Other aspects, features and advantages of the invention will be apparent from the following disclosure, including the detailed description of the invention and its preferred embodiments and the appended claims.

DESCRIPTION OF THE INVENTION

Various publications are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All publications cited herein are incorporated by reference as if set forth fully herein. It must be noted that as used herein and in the appended claims, the singular forms "a," "an," and "the" include plural reference unless the context clearly dictates otherwise.

Common or certain knowledge, scientific and medical terminologies can be readily found via internet, textbooks of chemistry, biochemistry, medicinal chemistry, pharmacology, dermatology and general medicine. The following are some examples. Robert K. Murray et al. eds. "Harper's Illustrated Biochemistry" 26$^{th}$ edn. Vol. I-II, McGraw Hill, 2003. Laurence L. Brunton et al. eds. "Goodman & Gilman's The Pharmacological Basis of Therapeutics" 12$^{th}$ edn. McGraw Hill Medical, 2011. Klaus Wolff et al. eds. "Fitzpatrick's Dermatology in General Medicine" 7$^{th}$ edn. Vol. I-II, McGraw Hill Medical, New York, 2008. Tony Burns et al. eds. "Rook's Textbook of Dermatology" 8$^{th}$ edn. Vol. I-IV, Wiley-Blackwell, 2010. Anthony S. Fauci et al. eds. "Harrison's Principles of Internal Medicine" 17$^{th}$ edn, McGraw Hill Medical, New York, 2008.

An amino acid is an organic acid having one or more than one alkaline radical such as amino, guanidino, imino, or hydrazine radical attached at any carbon atom other than carbon one. There are 20 common amino acids which are represented by chemical names, such as "glycine", or abbreviated symbols such as three letters, "Gly" or one letter "G". In this disclosure, three letters will be used. Except glycine, all other common amino acids have stereoisomers, i.e., enantiomer, D or L form. The amino acids in most natural peptides and proteins are all in L-form. Some D-form amino acids are produced by microorganisms or present in antibiotics, and have inhibitory or antagonistic actions. For example, D-alanine, D-aspartic acid, and D-glutamic acid are present in bacterial cell walls, and D-glutamic acid, D-aspartic acid and D-phenylalanine are present in the antibiotic bacitracin. An uncommon amino acid is an amino acid that is not a common amino acid. Examples of uncommon amino acids include, but are not limited to, (3-alanine and taurine. The uncommon amino acids can exist in D or L form.

The three letter symbols used for the 20 common amino acids are as follows: alanine (Ala), arginine (Arg), aspartic acid (Asp), asparagine (Asn), cysteine (Cys), glycine (Gly), glutamic acid (Glu), glutamine (Gln), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). In this disclosure, not all the common amino acids may be included in the N-acyldipeptide derivatives of the present invention.

The letter symbols used for uncommon amino acids are as follows: β-alanine (βAla), 4-aminobenzoic acid (Abz), aminobutanoic acid (Aba), γ-aminobutanoic acid (Gaba), β-aminoisobutanoic acid (Baia), 5-aminolevulinic acid (All), alliin (Ali), aminoadipic acid (Aaa), aminopimelic acid (Apa), 3-aminotyrosine (Atyr), canavanine (Cav), canaline (Can), ciliatine (Cil), cysteic acid (Cya), cysteine sulfinic acid (Csa), citruline (Cit), creatine (Cre), creatinine (Cm), 2,3-diaminosuccinic acid (Dsa), 2,4-diaminobutanoic acid (Dba), 2,3-diaminopropanoic acid (Dpa), 3,4-dihydroxyphenyl-alanine (Dopa), 3,5-diiodotyrosine (Dtyr), homoarginine (Har), homoserine (Hser), homocysteine (Hcys), homocitrulline (Hcit), 5-hydroxylysine (Hlys), 4-hydroxyproline (Hpro), 2-hydroxy-4-aminobutanoic acid (Haba), 3-hydroxy-4-aminobutanoic acid (Hyba), 4-hydroxyornithine (Horn), 4-hydroxyaspartic acid (Hasp), 4-hydroxyphenyl-glycine (Hpg), 3-iodotyrosine (Ityr), lanthionine (Lan), β-lysine (βLys), α-methylalanine (Mala), β-methylaspartic acid (Mas), 4-methylproline (Mpro), 2-methylserine (Mser), N-methylhistidine (Mhis), ornithine (Orn), phenylglycine (Pgly), 3-phenylserine (Pser), sarcosine (Sar), S-allyl-cysteine (Sac), theanine (The), thyroxine (Thy), 3,5,3'-triiodothyronine (Tth), and taurine (Tau). In this disclosure, not all the uncommon amino acids may be included in the N-acyldipeptide derivatives of the present invention.

The terms and abbreviations that can be used are as follows: acetyl, Ac; benzoyl, Bz; benzyl, Bzl; diphenylmethyl, Dpm; benzyl ester, OBzl; benzyloxycarbonyl, Z; t-butyl ester, OtBu; t-butyl, tBu; ethyl ester, OEt; formyl, For; hexyl ester, OHex; methyl ester, OMe; propanoyl, Pr; pyroglutamyl, Pyro; phenylacetyl, PhAc; and trityl, Trt.

A peptide bond, C(=O)NH, is a covalent bond formed between two amino acid molecules when the carboxyl group on one amino acid reacts with the amino group of the other amino acid in a dehydration synthesis reaction. A dipeptide is a peptide that contains two amino acid residues. Theoretically, 400 different dipeptides can be formed from 20 common amino acids, and more than 5,000 different dipeptides can be formed from both the common and uncommon amino acids. The dipeptides can be further modified by substitutions, etc. Each dipeptide can have different chemical and physical properties, and can have different biological and pharmacological actions.

When a particular group is "substituted", that group can have one or more substituents, preferably from one to five substituents, more preferably from one to three substituents, most preferably from one to two substituents, independently selected from the list of substituents.

With reference to substituents or amino acid residues in a peptide, the term "independently" means that when more than one of such substituents or amino acid residues are possible, such substituents or amino acid residues may be the same or different from each other.

As used herein, the term "subject" means any animal, preferably a mammal, most preferably a human, to whom will be or has been administered compounds or topical formulations according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human.

In one embodiment, "treatment" or "treating" refers to an amelioration, prophylaxis, or reversal of a disease or disorder, or at least one discernible symptom thereof. In another embodiment. "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, stabilization of a physical parameter, or both. In yet another embodiment, "treatment" or "treating" refers to delaying the onset of a disease or disorder.

In certain embodiments, compounds of interest are administered as a preventative measure. As used herein, "prevention" or "preventing" refers to a reduction of the risk of acquiring a given disease or disorder.

As used herein, a "therapeutically effective amount" of a compound of an embodiment of the present invention means the amount of the compound that elicits the biological or medicinal response in a tissue system, animal or human that is being sought by a researcher, veterinarian, medical doctor or other clinician, which includes alleviation of the symptoms of the disease or disorder being treated.

One skilled in the art will recognize that the therapeutically effective amount of a compound to be used in the instant invention can vary with factors, such as the particular subject, e.g., age, diet, health, etc., severity and complications and types of the symptom or disorder sought to be treated or prevented, the formulation used, etc.

According to one embodiment of the present invention, the N-acyldipeptide derivative of the present invention is represented by the following generic Formula (I):

R₁-AAB-AAC-R₂     Formula (I)

or an isomer, free acid, base, salt, lactone, amide, hydrazide, or ester thereof,
wherein $R_1$ is an acyl radical having up to 19 carbon atoms; AAB is an amino terminal amino acid residue selected from any amino acid; AAC is a carboxyl terminal amino acid residue selected from any amino acid; $R_2$ is $OR_3$, $NHR_4$ or $NHNHR_5$; $R_3$ is H, an alkyl, aralkyl or aryl radical having up to 19 carbon atoms; $R_4$ or $R_5$ is independently H, OH, an alkyl, aralkyl, aryl or acyl radical having up to 19 carbon atoms; a side chain of each of AAB and AAC optionally and independently has an extra functional radical selected from the group consisting of OH, SH, NHCONH₂, NHC(=NH)NH₂, NH₂, COOH, CONH₂, imidazolyl, pyrrolidinyl and indolyl; and the H or OH of the extra functional radical is optionally substituted by NH₂, an acyl, alkyl, aralkyl, or aryl radical having up to 19 carbon atoms. A typical acyl radical includes, but not limited to, acetyl (Ac), propanoyl (Pr), or benzoyl (Bz). A typical group attached to the carboxyl terminal amino acid residue includes, but not limited to, OH, OEt, NH₂, NHOH, or NHNH₂.

Preferably, AAB is an amino terminal amino acid residue selected from the group consisting of Ala, βAla, Abz, Asn, Cre, Cys, Dopa, Gly, Gln, Glu, Gaba, His, Hpg, Ile, Leu, Pgly, Phe, Pro, Ser, Trp, Tyr, and Val; and AAC is a carboxyl terminal amino acid residue selected from the group consisting of Ala, Cre, Cys, Dopa, Gly, His, Hpg, Ile, Leu, Lys, Pgly, Phe, Pro, Trp and Tyr.

Based on Formula (I), the N-acyldipeptide derivatives of the present invention can be divided according to the carboxyl terminal amino acid, which include, but are not limited to the following N-acyldipeptide derivatives:

1. N-Acetyldipeptide Derivatives (a) N-Acetyl alanine dipeptide derivatives, including, but not limited to: N—Ac-Ala-Ala-OH, N—Ac-Ala-Ala-OEt, N—Ac-Glu-Ala-OH, NH₂, N—Ac-Ile-Ala-OH, N—Ac-Leu-Ala-OH, N—Ac-Leu-Ala-NH₂, N—Ac-Val-Ala-OH, N—Ac-Val-Ala-NH₂, N—Ac-Cys-Ala-NH₂, N—Ac-Dopa-Ala-NH₂.

(b) N-Acetyl glycine dipeptide derivatives, including, but not limited to: N—Ac-β-Ala-Gly-NH₂, N—Ac-Asn-Gly-NH₂, N—Ac-Abz-Gly-NH₂, N—Ac-Cys-Gly-NH₂, N—Ac-Gaba-Gly-NH₂, NH₂, N—Ac-Ile-Gly-OH, N—Ac-Leu-Gly-NH₂, N—Ac-Leu-Gly-OH, N—Ac-Pro-Gly-NH₂, N—Ac-Ser-Gly-NH₂, N—Ac-Tyr-Gly-NH₂, N—Ac-Val-Gly-OH.

(c) N-Acetyl tyrosine dipeptide derivatives, including, but not limited to: N—Ac-Cys-Tyr-NH₂, N—Ac-Dopa-Tyr-NH₂, N,O,O'-Tri-Ac-Dopa-Tyr-NH₂, N,O,O'-Tri-Ac-Dopa-Tyr-OEt, N—Ac-Hpg-Tyr-NH₂, N—Ac-Tyr-Tyr-OH, N—Ac-Tyr-Tyr-OEt, N—Ac-Tyr-Tyr-NH₂, N—Ac-Ile-Tyr-OH, N—Ac-Leu-Tyr-OH, N—Ac-Leu-Tyr-NH₂, N—Ac-Val-Tyr-OH, N—Ac-Val-Tyr-NH₂, N—Ac-Tyr-Tyr-NHNH₂, N—Ac-Tyr-Tyr-NHNHAc.

(d) Other N-acyldipeptide derivatives, including, but not limited to: N—Ac-Arg-Cre-NH₂, N—Ac-Cre-Cre-NH₂, N—Ac-Cre-Cre-OH, N—Ac-Ser-Cre-NH₂, N—Ac-Tyr-Cre-NH₂, N—Ac-Cre-Tyr-NH₂, N—Ac-Cre-Ala-NH₂, N—Ac-Cys-Cys-NH₂, N—Ac-Cys-Cys-OH, N,O,O'-Tri-Ac-Dopa-Cys-OH, N,O,O'-Tri-Ac-Dopa-Cys-NH₂, N—Ac-Cys-O,O'-Di-Ac-Dopa-OH, N—Ac-Cys-O,O'-Di-Ac-Dopa-OEt, N—Ac-Dopa-Dopa-NH₂, N—Ac-Tyr-Dopa-NH₂, N—Ac-βAla-His-NH₂, N—Ac-βAla-1-MHis-NH₂, N—Ac-Ala-Ile-NH₂, N—Ac-Asp-Glu-NH₂, NH₂, N—Ac-Gaba-His-NH₂, N—Ac-Leu-Leu-NH₂, N—Ac-Tyr-Hpg-NH₂, N—Ac-βAla-His-OEt, N—Ac-Phe-Phe-NH₂, N—Ac-Trp-Trp-NH₂, N—Ac-Pgly-Pgly-NH₂, N—Ac-Hpg-Hpg-NH₂, N—Ac-Tyr-Tyr-NHOH, N—Ac-Val-Ala-NHOH, N—Ac-Glu-Lys-NH₂, and N—Ac-Gln-Lys-NH₂.

2. N-Propanoyldipeptide Derivatives.

(a) N-Propanoyl alanine dipeptide derivatives, including, but not limited to: N—Pr-Ala-Ala-OH, N—Pr-Ala-Ala-OEt, N—Pr-Ile-Ala-OH, N—Pr-Leu-Ala-OH, N—Pr-Leu-Ala-NH₂, N—Pr-Val-Ala-OH, NH₂.

(b) N-Propanoyl glycine dipeptide derivatives, including, but not limited to: N—Pr-Gly-Gly-OH, N—Pr-Gly-Gly-OEt, N—Pr-Gly-Gly-NH₂, N—Pr-Ala-Gly-NH₂, N—Pr-βAla-Gly-NH₂, N—Pr-Asn-Gly-NH₂, N—Pr-Cys-Gly-NH₂, N—Pr-Gln-Gly-NH₂, N—Pr-Gaba-Gly-NH₂, N—Pr-His-Gly-NH₂, N—Pr-Ile-Gly-OH, N—Pr-Ile-Gly-NH₂, N—Pr-Leu-Gly-OH, N—Pr-Leu-Gly-NH₂, N—Pr-Pro-Gly-NH₂, N—Pr-Ser-Gly-NH₂, N—Pr-Tyr-Gly-NH₂, N—Pr-Val-Gly-OH, N—Pr-Val-Gly-NH₂.

(c) N-Propanoyl tyrosine dipeptide derivatives, including, but not limited to: N—Pr-Tyr-Tyr-OH, N—Pr-Tyr-Tyr-OEt, N—Pr-Tyr-Tyr-NH₂, N—Pr-Ile-Tyr-OH, N—Pr-Ile-Tyr-NH₂, N—Pr-Leu-Tyr-OH, N—Pr-Leu-Tyr-NH₂, N—Pr-Val-Tyr-OH, N—Pr-Val-Tyr-NH₂, N—Pr-Tyr-Tyr-NHNH₂, N—Pr-Tyr-Tyr-NHNHPr, N—Pr-Dopa-Tyr-NH₂, N—Pr-Cys-Tyr-NH₂.

(d) Other N-propanoyldipeptide derivatives, including, but not limited to: N—Pr-Glu-Glu-OH, N—Pr-Glu-Glu-OEt, N—Pr-Glu-Glu-NH₂, N—Pr-Glu-Ala-OH, N—Pr-Glu-Ala-NH₂, N—Pr-βAla-His-NH₂, N—Pr-βAla-1-MHis-NH₂, N—Pr-Ala-Ile-NH₂, N—Pr-Asp-Glu-NH₂, N—Pr-Gly-Gln-NH₂, N—Pr-Gaba-His-NH₂, N—Pr-Leu-Leu-OH, N—Pr-Leu-Leu-OEt, N—Pr-Leu-Leu-NH₂, N—Pr-Gly-Ile-NH₂, N—Pr-Ile-Ile-OH, N—Pr-Ile-Ile-NH₂, N—Pr-βAla-His-OEt, N—Pr-Cys-Cys-NH₂, N—Pr-Dopa-Dopa-NH₂, N—Pr-Dopa-Cys-NH₂, N—Pr-Cys-Dopa-NH₂, N—Pr-Phe-Phe-NH₂, N—Pr-Trp-Trp-NH₂, N—Pr-Glu-Lys-NH₂, and N—Pr-Gln-Lys-NH₂.

The preferred bioactive dipeptide derivative of the present invention is selected from the group consisting of N—Ac-Ile-Ala-NH₂, N—Ac-Leu-Ala-NH₂, N—Ac-Val-Ala-NH₂, N—Ac-Cys-Cys-NH₂, N—Ac-Tyr-Cys-NH₂, N—Ac-Dopa-Dopa-NH₂, N—Ac-Ile-Gly-NH₂, N—Ac-Leu-Gly-NH₂, N—Ac-Val-Gly-NH₂, N—Ac-Tyr-Tyr-NH₂, N—Ac-Cys-Tyr-NH₂, N—Ac-Ile-Ala-OH, N—Ac-Leu-Ala-OH, N—Ac-Val-Ala-OH, N—Ac-Cys-Cys-OH, N—Ac-Tyr-Cys-OH, N—Ac-Dopa-Dopa-OH, N—Ac-Ile-Gly-OH, N—Ac-Leu-Gly-OH, N—Ac-Val-Gly-OH, N—Ac-Tyr-Tyr-OH, N—Ac-Cys-Tyr-OH, N—Pr-Ile-Ala-NH₂, N—Pr-Leu-Ala-NH₂, N—Pr-Val-Ala-NH₂, N—Pr-Cys-Cys-NH₂, N—Pr-Tyr-Cys-NH₂, N—Pr-Dopa-Dopa-NH₂, N—Pr-Ile-Gly-NH₂, N—Pr-Leu-Gly-NH₂, N—Pr-Val-Gly-NH₂, N—Pr-Tyr-Tyr-NH₂, N—Pr-Cys-Tyr-NH₂, N—Pr-Ile-Ala-OH, N—Pr-Leu-Ala-OH, N—Pr-Val-Ala-OH, N—Pr-Cys-Cys-OH, N—Pr-Tyr-Cys-OH, N—Pr-Dopa-Dopa-OH, N—Pr-Ile-Gly-OH, N—Pr-Leu-Gly-OH, N—Pr-Val-Gly-OH, N—Pr-Tyr-Tyr-OH, and N—Pr-Cys-Tyr-OH.

The more preferred bioactive dipeptide derivative of the present invention is selected from the group consisting of N—Ac-Ile-Ala-NH$_2$, N—Ac-Leu-Ala-NH$_2$, N—Ac-Val-Ala-NH$_2$, N—Ac-Cys-Cys-NH$_2$, N—Ac-Tyr-Cys-NH$_2$, N—Ac-Dopa-Dopa-NH$_2$, N—Ac-Ile-Gly-NH$_2$, N—Ac-Leu-Gly-NH$_2$, N—Ac-Val-Gly-NH$_2$, N—Ac-Tyr-Tyr-NH$_2$, N—Ac-Cys-Tyr-NH$_2$, N—Ac-Ile-Ala-OH, N—Ac-Leu-Ala-OH, N—Ac-Val-Ala-OH, N—Ac-Cys-Cys-OH, N—Ac-Tyr-Cys-OH, N—Ac-Dopa-Dopa-OH, N—Ac-Ile-Gly-OH, N—Ac-Leu-Gly-OH, N—Ac-Val-Gly-OH, N—Ac-Tyr-Tyr-OH, and N—Ac-Cys-Tyr-OH.

The most preferred bioactive dipeptide derivative of the present invention is selected from the group consisting of N—Ac-Ile-Ala-NH$_2$, N—Ac-Leu-Ala-NH$_2$, N—Ac-Cys-Cys-NH$_2$, N—Ac-Tyr-Cys-NH$_2$, N—Ac-Dopa-Dopa-NH$_2$, N—Ac-Leu-Gly-NH$_2$, N—Ac-Tyr-Tyr-NH$_2$, and N—Ac-Cys-Tyr-NH$_2$.

N-acyldipeptide derivatives according to embodiments of the present invention can be made by any method known to those skilled in the art in view of the present disclosure.

Chemical and physical properties, biological functions and therapeutic effects of a peptide depend exclusively on the nature and sequence of amino acid residues, and different amino acid residues or a different amino acid sequence may result in a completely different peptide. In addition to chemical and physical properties, biological functions and therapeutic effects of a peptide are also changed when the functional groups of such peptide are modified by substitution. In most cases, the bioactive dipeptide derivative of the present invention has different and much improved chemical and physical properties, biological functions and therapeutic effects as compared to an unmodified peptide.

A peptide is usually an amphoteric substance, having positive and negative charges in the same molecule. A peptide normally cannot penetrate the skin on topical application because of the tough stratum corneum layer that acts as a permeation barrier. In general, an ionic substance or any substance with a molecular weight of more than 800 daltons cannot readily penetrate the intact skin. The N-acyldipeptide derivatives of the present invention have the alkaline radical such as an amino group modified by acylation, so that they are no longer amphoteric in nature, and are readily bioavailable for penetration and/or distribution to target tissues or sites for pharmacological actions by topical or systemic administration.

Another general aspect of the present invention relates to a method of treating or preventing a disease, symptom or syndrome associated with immune, tumors, cancers, nervous, vascular, musculoskeletal, cutaneous system, or other tissues and systems in a subject in need of the treatment. The method comprises topically or systemically administering to the subject a composition comprising a therapeutically effective amount of an N-acyldipeptide derivative according to an embodiment of the present invention and a pharmaceutically or cosmetically acceptable carrier.

Conditions, disorders, symptoms and syndromes associated with the (A) tumors and cancers, (B) immune system, (C) nervous system, (D) vascular system, (E) musculoskeletal system, (F) cutaneous system, and (G) other tissues or systems that can be treated with a composition of the present invention are described as follows.

(A) Tumors and Cancers

Cancer is an unregulated proliferation of cells due to loss of normal controls, resulting in abnormal growth, lack of differentiation, local tissue invasion, and often, metastasis. Tumor is an abnormal growth of cells or tissues which may be benign or malignant. Tumors or cancers that can be treated with a composition of the present invention include, but are not limited to, actinic keratosis, adrenal cancer, basal cell carcinoma, bladder cancer, brain tumor, breast cancer, cervical cancer, colon cancer, esophagus cancer, head and neck cancer, Hodgkin's disease, Kaposi's sarcoma, larynx cancer, leukemia, lung carcinoma, liver cancer, melanoma, multiple myeloma, mesothelioma, ovarian cancer, pancreatic cancer, prostate cancer, renal cancer, rectal cancer, stomach cancer, squamous cell carcinoma, thyroid cancer, testicular cancer, thyroid cancer, and uterine cancer. Breast cancer most often involves glandular breast cells in the ducts or lobules, and can invade locally and spread through lymph nodes and bloodstream, then to lungs, liver, bone, brain and skin. Lung carcinoma is a leading cause of lung cancer with symptoms of coughing, chest discomfort or pain, and weight loss. Liver cancer is usually hepatocellular carcinoma often resulting from liver cirrhosis. Pancreatic cancer, primarily ductal adenocarcinoma, has symptoms of weight loss, abdominal pain, and jaundice. Brain tumors such as gliomas, medulloblastomas and ependymomas can have symptoms of headache, pain, edema, etc.

The development and growth of tumors and cancers can be due to deranged immune system even though the tumors or cancers may be caused by mutations.

(B) Immune System

The immune system, very similar to organs such as liver, kidney and thyroid, is composed of specialized cells that play a vital role in host defense. These cells include leukocytes (white blood cells) and dendritic cells. The leukocytes are divided into granulocytes (65%), specific granules in the cytoplasm such as neutrophils, eosinophils, and basophils; and agranulocytes, no specific granules in the cytoplasm such as lymphocytes (25-35%) and monocytes (5-10%). The lymphocytes are subdivided into B lymphocytes (antibody production) and T lymphocytes (foreign agent and tissue destruction). The monocyte can migrate from blood to tissue, and become a macrophage. The dendric cell is derived from bone marrow and is critical in activation and priming of the lymphocyte.

Deranged immune system can cause the following disorders:

(1) Rheumatic, connective tissue or collagen diseases. These diseases include, but are not limited to, systemic lupus erythematosus, rheumatoid arthritis, seronegative spondylarthritides (ankylosing spondylitis), Sjogren's syndrome (keratoconjunctivitis sicca, xerostomia), systemic sclerosis, polymyositis and dermatomyositis.

(2) Endocrine autoimmune diseases. These diseases include, but are not limited to, Type 1 diabetes, autoimmune thyroid disease such as Graves' disease and Hashimoto's thyroiditis, and Addison's disease.

(3) Liver diseases. These diseases include, but are not limited to, autoimmune hepatitis, sclerosing cholangitis, biliary cirrhosis, viral hepatitis including hepatitis A, hepatitis B, and hepatitis C.

(4) Gastrointestinal diseases. These diseases include, but are not limited to, mucosal disorder, atrophic gastritis, pernicious anemia, inflammatory bowel disease, and allergic food reactions.

(5) Immune mediated nephritis and vasculitis. These diseases include, but are not limited to, glomerulonephritis, Wegener's granulomatosis, microscopic polyarteritis, and cryoglobulinanemia.

(6) Immune mediated skin diseases. These diseases include, but are not limited to, psoriasis, vitiligo, bullous pemphigoid, pemphigus vulgaris, and pemphigus foliaceus.

(7) Immune mediated diseases of nervous system and eye. These diseases include, but are not limited to, multiple sclerosis, Guillain-Barre syndrome, myasthenia gravis, Lambert-Eaton syndrome, stiff man syndrome, keratitis, keratoconjunctivitis sicca, scleritis, episcleritis, and uveitis.

(8) Human immunodeficiency virus (HIV) and acquired immune deficiency syndrome (AIDS). HIV is a member of retrovirus family, with a single-stranded RNA genome. Such RNA genome can encode the enzyme reverse transcriptase, capable of transcribing viral RNA into DNA, and allowing the virus to integrate into the host cell genome. During the initial stage of infection, the virus targets memory CD4 T lymphocytes as a receptor, and depletes CD4 T cells from gut and peripheral lymph nodes. The immunity from B lymphocytes, dendritic cells and macrophages is also weakened. The vaccine remains the best hope of controlling HIV infection, however, there are numerous issues to be resolved for an effective, inexpensive and safe immunization against HIV infection. The challenging issues are (a) the virus can survive and be transmitted within a host and between hosts in extracellular form, as blood borne virus particles, and also in intracellular form hidden within infected host cells, (b) the virus copies its genome into host cells, and live attenuated virus vaccine may pose a safety issue, (c) the virus has multiple strains and a very high mutability which is challenging for a vaccine using fixed virus sequences, and may not be effective for other strains, (d) there is no small animal model existing for HIV infection, and the efficacy studies carried out for non-human primates are rather expensive.

Other deranged immune system may also involve the growth and spread (metastasis) of tumors and cancers.

(C) Nervous System

The conditions, disorders, symptoms and syndromes associated with the nervous system include, but are not limited to, the following conditions or disorders, which may present as indicated, or otherwise: (1) dementia and Alzheimer's disease: progressive loss of memory, shrinkage and atrophy of cerebral cortex, tangles of fibers in nerve cells, senile plaques of β-amyloid, decreased choline acetyltransferase enzyme; (2) carpal tunnel syndrome: weakness, pain, tingling, numbness, burning in palm and fingers; (3) encephalitis: inflammation of the brain; (4) headache: migraine, expansion of blood vessels pressing on nerves or constriction blocking blood supply, inflammation, muscle contraction to face, neck or scalp; (5) meningitis: infection of spinal fluid and meninges; (6) neuralgia: nerve pain, peripheral neuropathy, sciatica, shingles, trigeminal neuralgia; (7) Parkinson's disease: tremors in limbs, muscular rigidity; (8) amnesia: loss of memory and inability to form new memory; and (9) others, such as ataxia, Bell's palsy, epilepsy, multiple sclerosis, myasthenia gravis, narcolepsy, paralysis and rabies.

Alzheimer's disease causes progressive cognitive deterioration and is characterized by senile plaques of β-amyloid deposits, neurofibrillary tangles in the cerebral cortex and subcortical gray matter, and currently there is no cure.

Parkinson's disease is an idiopathic, slowly progressive, degenerative central nervous system (CNS) disorder characterized by resting tremor, muscular rigidity, slow and decreased movement, and postural instability, and currently there is no cure.

(D) Vascular System

The vascular conditions, reactions and disorders that can be treated with a composition of the present invention include, but are not limited to, acanthosis nigricans, acrocyanosis, actinic cheilitis, actinic prurigo, dermatitis, dermatosis, dermographism, dyshidrosis, drug eruptions, inflammation, or eczema, erythema, erythema migrans, erythrocyanosis, erythromelalgia, familial hemorrhage, histamine reaction, inflammatory papular and pustular lesions, lichen planus, lupus erythematosus, mycosis fungoides, neurodermatitis, neuropeptide and neurovascular reactions, parapsoriasis, perniosis (chilblains), photoallergy, photoreaction, photosensitivity, pityriasis rosea, pityriasis rubra pilaris, polymorphic light eruption, psoriasis, rhinophyma, rosacea, sclerosis, spider naevi, T-cell disorders, telangiectasia, varicose veins (varicosis), urticaria, vessel dilation, and other vascular reactions.

(E) Musculoskeletal System

The conditions or abnormalities of musculoskeletal system include, but are not limited to, the following conditions or disorders, which may present as indicated, or otherwise: (1) osteoporosis: reduction of calcium in bone leading to thin bone and bone susceptible to fracture; (2) osteoarthritis: inflammation of joint cartilage provoking swelling and pain; (3) rheumatoid arthritis: inflammation of synovium and destruction of cartilage, damage to heart, lungs, nerves and eyes; (4) ankylosing spondylitis: arthritis affecting sacroiliac joints and spine with inflammation and immovability; (5) bursitis: inflammation of bursa; (6) tendinitis: inflammation of tendon; (7) gout: recurrent acute arthritis from uric acid deposit; and (8) specifically, neck, shoulder, elbow, wrist, lower back, hip, knee and ankle pains, inflammation, and arthritis.

(F) Cutaneous System and Others

The cosmetic, dermatological or other conditions and disorders of cutaneous system that can be treated with a composition of the present invention include, but are not limited to, infections, deranged or disordered cutaneous or mucocutaneous tissue relevant to skin, nail and hair; oral, vaginal and anal mucosa; disturbed keratinization; inflammation; changes associated with intrinsic and extrinsic aging, and others which may or may not be related to cutaneous system. The manifestations include, but are not limited to, oily skin; acne; rosacea; age spots; blemished skin; blotches; cellulite; dermatoses; dermatitis; skin, nail and hair infections; dandruff; dryness or looseness of skin, nail and hair; xerosis; inflammation, or eczema; elastosis; herpes; hyperkeratosis; hyperpigmented skin; ichthyosis; keratoses; lentigines; melasmas; mottled skin; pseudofolliculitis barbae; photoaging and photodamage; pruritus; psoriasis; skin lines; stretch marks; thinning of skin, nail plate and hair; warts; wrinkles; oral or gum disease; irritated, inflamed, red, unhealthy, damaged or abnormal mucosa, skin, hair, nail, nostril, ear canal, anal or vaginal conditions; breakdown, defective synthesis or repair of dermal components; abnormal or diminished synthesis of collagen, glycosaminoglycans, proteoglycans and elastin, as well as diminished levels of such components in the dermis; uneven skin tone; uneven and rough surface of skin, nail and hair; loss or reduction of skin, nail and hair resiliency, elasticity and recoilability; laxity; lack of skin, nail and hair lubricants and luster; fragility and splitting of nail and hair; yellowing skin; reactive, irritating or telangiectatic skin; and dull and older-looking skin, nail and hair. In addition, the composition of the current invention can be used for general care of skin, nail and hair; to improve skin texture and pores, flakiness and redness; to make skin soft, smooth, fresh, balanced, visibly clear, even-toned and brighter; to increase skin fullness and plumpness; and for skin bleach and lightening and wound healing; to reduce or prevent sweating or perspiration of underarm, crotch, palm, or other parts of the body.

Skin, nail and hair infections can be caused by microorganisms which include bacteria, fungi, yeasts, molds, parasites and viruses. More specifically, the bacterial infections can cause trichomycosis axillaris, pitted keratolysis, erythrasma, impetigo, ecthyma, furunculosis (boils), carbuncle, scalded skin syndrome, toxic shock syndrome, erysipelas, cellulitis, necrotizing fasciitis, erysipeloid, cat-scratch disease (*Rochalimaea henselae*), syphilis, lyme disease (*Borrelia burgdorferi*), cutaneous anthrax (*Bacillus anthracis*), gonococcal septicaemia, inoculation tuberculosis, scrofuloderma, tuberculides, erythema induratum, leprosy (*Mycobacterium leprae*), leishmaniasis and acute paronychia. The viral infections can cause viral warts (human papilloma virus), varicella (chickenpox), herpes zoster (varicella-zoster), herpes simplex (herpesvirus hominis), molluscum contagiosum, orf, AIDS (acquired immunodeficiency syndrome, human immunodeficiency virus, HIV), herpangina, mucocutaneous lymph node syndrome (Kawasaki's disease), Gianotti-Crosti syndrome (hepatitis B virus), measles, rubella and erythema infectiosum. The fungal infections can cause ringworm, tinea pedis (athlete's foot), tinea unguis (nail infection), tinea hands, tinea groin, tinea trunk and limbs, tinea capitis (scalp), oral candidiasis, candida intertrigo, genital candidiasis, chronic paronychia, chronic mucocutaneous candidiasis, pityriasis versicolor, histoplasmosis, coccidioidomycosis, blastomycosis, sporotrichosis, actinomycosis and mycetoma (madura foot).

(G) Other Tissues or Systems

These conditions and diseases include vision disorders of eyes, vocal desfunctions, gum and periodontal diseases, hearing loss, sexual dysfunctions, desired augmentation of breast and penis, and increased body strength. Aside from cataract and glaucoma, the vision disorders can be due to near-sightedness (myopia) and far-sightedness (hyperopia). Enhanced strength of extrinsic and intrinsic eye muscles, along with increased relaxation of eye nerves may help improve conditions of myopia and hyperopia.

Weakness and poor quality of the voice can be caused by larynx dysfunction. Relaxation of laryngeal nerves and enhanced laryngeal muscle may help improve the quality and the strength of voice.

The preferred condition or disease to be treated according to embodiments of the present invention is selected from the group consisting of arthritis, cancer, immune, infections, inflammation, musculus, nerve, skin, and vasculature.

The more preferred condition or disease to be treated is selected from the group consisting of arthritis, Alzheimer's disease, aging related skin changes, age spots, breast cancer, cellulitis, dermatitis, dermatoses, dry skin, eczema, itch, infections, inflammation, joint disorder, mottled skin, muscle disorder, pain, Parkinson's disease, photoaging, psoriasis, rosacea, stretch marks, varicose veins, viral infections, wrinkles, for skin lightening, to enhance muscle strength, and to reduce or prevent sweating or perspiration of underarm, crotch, palm, or other parts of the body.

The most preferred condition or disease to be treated is selected from the group consisting of arthritis, aging related skin changes, age spots, cellulitis, dermatitis, dermatoses, eczema, itch, inflammation, joint disorder, mottled skin, rosacea, stretch marks, wrinkles, for skin lightening, and to reduce or prevent sweating or perspiration of underarm, crotch, palm or other parts of the body.

Physiological Functions, Pharmacological Actions and Therapeutic Effects

When a substance is found to modulate or normalize certain physiological functions, the resulted pharmacological actions can provide broad therapeutic effects on related conditions, disorders, diseases, symptoms and syndromes; simply described as "related indications". Therefore, the related indications can be grouped into one single physiological function as follows.

(1) Disturbed Keratinization (DK).

Many skin disorders such as dry skin, ichthyosis, calluses, keratosis and acne (initiated by blackhead formation) are due to disturbed keratinization (disturbed or abnormal skin formation). When a substance is discovered to modulate or normalize keratinization, the substance is reasonably expected or predicted to improve those conditions or disorders which are caused by a common cause of disturbed keratinization.

Therefore, disturbed keratinization covers, but is not limited to dry skin; dryness or looseness of skin, nail and hair; xerosis; ichthyosis; calluses; keratoses; acne; rosacea; blemished skin; dandruff; uneven skin tone; uneven and rough surface of skin; abnormal skin texture and pores; flakiness and redness; and to improve or make skin soft, smooth, fresh, balanced, or visibly clear.

(2) Aging Related Changes of Skin, Nail and Hair (AG).

In "Rook's Textbook of Dermatology" by Burns et al. Wiley-Blackwell, 2010, Vol. 1, page 8.22 under "The ageing skin", it is described that "wrinkling of ageing skin is almost entirely the result of changes in the dermis". In fact, skin aging including wrinkles is due mainly to progressive degeneration of dermal components; namely, glycosaminoglycans (GAGs), collagen and elastic fibers in the dermis. In a publication by Ditre et al. J. Amer Acad Dermatol, 1996, pages 187-195, under "Effects of α-hydroxy acids on photoaged skin: A pilot clinical, histologic, and ultrastructural study", histologic and ultrastructural studies show that skin plump or increased skin thickness caused by topical application of a substance results from a combination of epidermal and dermal changes. In epidermal changes, the epidermis increases in thickness, and the melanin pigmentation shows less clumping of melanin resulting in lighter skin color and improved age spots. In dermal changes, there are increased amounts of both glycosaminoglycans (GAGs) and collagen fibers, and elastic fibers tend to be longer and thicker. Therefore, when a substance is found to plump or increase the skin thickness, the substance is reasonably expected or predicted to improve aging related skin changes including fine lines, wrinkles, photoaging, age spots, blotches, hyperpigmented skin, mottled skin, and for younger-looking skin and skin lightening.

In general, aging related skin changes covers, for example, fine lines; wrinkles; age spots; blotches; cellulite; elastosis; lentigine; mottled skin; photoaging and photodamage; stretch marks; thinning of skin, nail plate and hair; warts; wrinkles; breakdown, defective synthesis or repair of dermal components; abnormal or diminished synthesis of collagen, glycosaminoglycans, proteoglycans and elastin, as well as diminished levels of such components in the dermis; loss or reduction of skin, nail and hair resiliency, elasticity and recoilability; laxity; lack of skin, nail and hair lubricants and luster; fragility and splitting of nail and hair; yellowing skin; and dull and older-looking skin, nail and hair, even-toned and brighter; to increase skin fullness and plumpness.

(3) Deranged Immune Disorders and Inflammation (DI).

The deranged or disturbed immune disorders can cause inflammation, pain, itch, swelling, edema, dermatitis, eczema, psoriasis, dermatoses, joint disorders, and arthritis. When a substance is found to modulate or normalize activities of immune cells by reducing inflammation, the substance is reasonably expected or predicted to improve the related indications or disorders.

Therefore, the deranged immune disorders cover, for example, inflammatory disorders; inflammation, dermatitis, or eczema; psoriasis; dermatoses; painful joints; arthritis; infections; Type 1 diabetes; viral hepatitis; inflammatory bowel disease; allergic food reactions; nephritis; vasculitis; vitiligo; multiple sclerosis; HIV and AIDS.

(4) Tumors and Cancers (CA).

Most tumors and cancers are caused by unregulated proliferation of cells due to loss of normal controls, resulting in abnormal growth, lack of differentiation, local tissue invasion, and often, metastasis. When a substance is found to normalize the control of cell growth, the substance is reasonably expected or predicted to improve or eradicate most types of tumors and cancers including skin tumors and cancers, breast cancer, lung carcinoma, liver cancer, pancreatic cancer, colon cancers, and brain tumors.

Therefore, tumors and cancers cover: adrenal cancer, anus cancer, brain tumor and cancer, bladder cancer, breast cancer, cervix cancer, colon cancers, endometrium cancer, esophagus cancer, Kaposi sarcoma, kidney cancer, larynx cancer, leukemia, lymphoma, lung cancer, liver cancer, oral cavity cancer, ovarian cancer, prostate cancer, pancreatic cancer, rectum cancer, skin cancer, stomach cancer, testis cancer, thyroid cancer, and uterine cancer.

(5) Nerve Disorders (ND).

Nervous system is very complex initiating from the brain, and controlling almost all the body functions. Only the dead cells or dead tissues such as nails, hair and stratum corneum do not contain nerve fibers. Loss or malfunction of nerve cells can result in various nerve disorders, symptoms and syndromes.

Therefore, nerve disorders cover: dementia, Alzheimer's disease: progressive loss of memory, carpal tunnel syndrome, weakness, pain, tingling, numbness, burning in palm and fingers, encephalitis, headache, migraine, meningitis, neuralgia, peripheral neuropathy, sciatica, Parkinson's disease, amnesia, Bell's palsy, epilepsy, multiple sclerosis, paralysis and headache.

In view of the present disclosure, standard procedures can be performed to evaluate the effect of the administration of a composition to a subject, thus allowing a skilled artisan to determine the therapeutically effective amount of the compound.

The clinically observable beneficial effect can be a situation, that, when a composition of the present invention is administered to a subject after symptoms to be treated are observable, the symptoms are prevented from further development or aggravation, or develop to a lesser degree than without administration of the specified composition according to embodiments of the present invention. The clinically observable beneficial effect can also be that, when a composition of the present invention is administered to a subject before symptoms to be treated are observable, the symptoms are prevented from occurring or subsequently occur to a lesser degree than without administration of the composition of the present invention.

In one embodiment, a therapeutically effective amount of the N-acyldipeptide derivative will reduce a syndrome or a condition of discomfort of the subject to be treated by at least about 20%, for example, by at least about 30%, about 40%, about 50%, about 60%, about 70%, about 80%, about 90%, or about 100%.

In another embodiment, a therapeutically effective amount of the N-acyldipeptide derivative will prevent a syndrome or a condition of discomfort of the subject to be treated, or reduce the probability of its onset by at least about 20%, for example, by at least about 30%, about 40%, about 50%, about 60%, about 70%, about 80%, about 90%, or about 100%.

Dosages and dosing frequency will be determined by a trained medical professional depending on the activity of the compounds used, the characteristics of the particular topical formulation, and the identity and severity of the dermatologic disorder treated or prevented.

Administration Routes and General Preparations

Another general aspect of the present invention relates to a composition for systemic or topical administration to a subject, the composition comprising a therapeutically effective amount of an N-acyldipeptide derivative according to an embodiment of the present invention and a pharmaceutically or cosmetically acceptable carrier. Compositions according to embodiments of the present invention can be formulated in any manner suited for topical or systemic administration to a subject.

Compositions comprising a bioactive dipeptide derivative of the present invention can be administered to a subject in need by topical application, systemic or other routes. The topical application includes skin, eye, mucous membranes of the conjunctiva, nasopharynx, oropharynx, vagina, urethra, rectum, and anus. The systemic administration includes oral (enteral) administration and parenteral injections. The parenteral injections include intravenous injection or infusion, intra-arterial injection, subcutaneous injection, intramuscular injection, and intra-articular injection. Other routes of administration include sublingual administration, under the tongue, from oral mucosa bypassing the portal circulation, and pulmonary adsorption by inhaling and absorbing through the respiratory tract.

For topical application, the composition comprising a bioactive dipeptide derivative of the present invention can be formulated as solution, gel, lotion, cream, oil-in-water emulsion, water-in-oil emulsion, ointment, shampoo, spray, stick, powder, mask, pads, mouth rinse or wash, vaginal gel or suppositories, rectal gel or suppositories, urethral gel or suppositories or other form acceptable for use on skin, nail, hair, oral mucosa, vaginal or anal mucosa, mouth or gums. The concentration of an active ingredient can be about 0.001% to about 99.9% by weight or volume (solution composition) of the total composition, with preferred concentration of about 0.01% to about 30%, and with more preferred concentration of about 0.1% to about 10% by weight or by volume (solution composition) of the total composition.

A typical gel composition may be formulated by the addition of a gelling agent, such as chitosan, methyl cellulose, ethyl cellulose, polyvinyl alcohol, poly quaterniums, hydroxyethylcellulose, hydroxypropylcellulose, hydroxypropylmethylcellulose, carbomer or ammoniated glycyrrhizinate to a solution comprising the N-acyldipeptide derivative. The preferred concentration of the gelling agent may range from 0.1 to 4 percent by weight of the total composition. In the preparation of shampoo, the N-acyldipeptide derivative may be first dissolved in water or propylene glycol, and the solution thus obtained may be mixed with a shampoo base. Concentrations of the N-acyldipeptide derivative used in gel or shampoo form are the same as described above.

To prepare a solution composition, at least one bioactive dipeptide derivative of the present invention is dissolved in a solution prepared from water, ethanol, propylene glycol, butylene glycol, or other topically acceptable solvent. To prepare a topical composition, a bioactive dipeptide derivative of the present invention can be incorporated as a fine powder form without dissolving, or first dissolving in water, ethanol, propylene glycol or other solvent, and the solution thus obtained is mixed with a topically acceptable base or vehicle including gel, lotion, cream, oil-in-water emulsion, water-in-oil emulsion, ointment, shampoo, spray, stick, powder, mask, pads, mouth rinse or wash, vaginal gel or suppositories, and rectal gel or suppositories. Contemplated embodiments of the present invention include concentration ranges of 0.001% to 0.01%, 0.01% to 0.1%, 0.1% to 0.2%, 0.2% to 0.3%, 0.3% to 0.4%, 0.4% to 0.5%, 0.5% to 0.6%, 0.6% to 0.7%, 0.7% to 0.8%, 0.8% to 0.9%, 0.9% to 1%, 1% to 2%, 2% to 3%, 3% to 4%, 4% to 5%, 5% to 6%, 6% to 7%, 7% to 8%, 8% to 9%, 9% to 10%, 10% to 14%, 14% to 18%, 18% to 22%, 22% to 26%, 26% to 30%, 30% to 35%, 35% to 40%, 40% to 45%, 45% to 50%, 50% to 60%, 60% to 70%, 70% to 80%, 80% to 90%, and 90% to 99.9% by weight or volume of the total composition.

The choice of topically administrable composition will depend on several factors, including the nature of the symptoms to be treated or prevented, the physiochemical characteristics of the particular compound to be administered and of other excipients present, their stability in the formulation, available manufacturing equipment, and cost constraints.

For systemic use or other routes of administration, a bioactive dipeptide derivative of the present invention can be formulated for oral administration, parenteral injections or other routes including oral mucosa, under the tongue administration with or without pharmaceutically acceptable vehicle or carrier.

In oral preparations, a bioactive dipeptide derivative of the present invention is formulated in powder, tablet form, gelatin capsules with or without mixing with gelatin powder, or in other form including a liquid or suspension form. Each tablet, capsule or unit dosage contains about 0.01 mg to about 100 mg, preferably about 0.1 mg to about 50 mg, and more preferably about 1 mg to about 25 mg of the bioactive dipeptide derivative. As an illustration, bioactive dipeptide derivative powder, 1 mg, can be placed under the tongue without swallowing for a short time to achieve systemic administration. The daily dosage for a subject can vary, however in general is about 0.001 mg/kg to about 10 mg/kg, preferably about 0.01 mg to about 5 mg/kg, and more preferably about 0.1 mg to about 2 mg/kg body weight of the subject.

For parenteral injections, a bioactive dipeptide derivative is prepared in a solution or suspension under sterilized conditions in concentration from about 0.01% to about 10%, preferably about 0.1% to about 5%, more preferably about 0.2% to about 2% weight by volume in water, propylene glycol, glycerol, polyethylene glycol, a mixture thereof, or in other vehicle or carrier. The other vehicle or carrier includes peanut oil, soybean oil, mineral oil, sesame oil, and the like. As an option, a thickener can be added into an injection composition to increase the viscosity, so that the composition has a comparable viscosity with the body fluid in the knee joints or other joints. As an illustration, but not limitation, the thickener can be selected from the group consisting of carboxymethylcellulose, sodium carboxymethylcellulose, casein, cellulose, gelatin, sodium hyaluronate, methylcellulose, PEG 200, PEG 300, PEG 400, PEG 600, PEG 3350, PEG 4000, polyglactin, polylactide, polypropylene glycol, polyvinyl alcohol, protamine sulfate, povidone, starch, captisol, dextran, dextrose, fructose, albumin, and lactose.

In another embodiment, the composition may further comprise an additional cosmetic, pharmaceutical, or other agent to achieve synergetic or synergistic effects. To prepare a topical combination composition, a cosmetic, pharmaceutical or other agent is incorporated into any one of the above compositions by dissolving or mixing the agent into the formulation. Other forms of compositions for delivery of the N-acyldipeptide derivative of the present invention are readily recognized by those skilled in the art.

A composition comprising the N-acyldipeptide derivative may be taken orally one to three times, preferably twice daily, for prevention or treatment of disorders and diseases associated with immune, tumors, cancers, nervous, vascular, musculoskeletal, cutaneous system, or other tissues and systems. The oral administration may continue until the symptom or disease has been eradicated or substantially improved. The symptoms or disorders include, for example, pains, pruritus, inflammation, erythema, dermatitis, acne, eczema, dementia, Alzheimer's disease, joint pain or swelling, and arthritis.

The bioactive dipeptide derivative of the present invention is believed to be therapeutically effective to alleviate or improve conditions, disorders, diseases, symptoms or syndromes associated with immune, nervous, vascular, musculoskeletal, cutaneous system, other tissues and systems, or for regulation and treatment of abnormal cell growth including tumors and cancers. The composition containing a bioactive dipeptide derivative of the present invention can be administered alone or in combination with another active agent. The composition and the other active agent can be administered simultaneously or sequentially.

Other forms of compositions for delivery of the compound of the present invention are readily blended, prepared or formulated by those skilled in the art.

A composition comprising a bioactive dipeptide derivative is administered to a subject in various means that are acceptable for the conditions to be treated.

In one embodiment, the composition was topically applied to the skin. For example, a solution or cream containing 0.1% to 1% by weight of N-acyldipeptide or N-acyldipeptide amide, such as N—Ac-L-Tyr-L-Tyr-NH$_2$, or N—Ac-L-Val-L-Ala-NH$_2$ was topically applied to an involved skin once or twice daily for several weeks or until a desired therapeutic effect had been achieved.

The composition can also be administered systemically or by other routes, such as via oral administration or parenteral injection. For example, N—Ac-L-Val-L-Ala-NH2 0.2% (w/w) in water, 1 ml (2 mg) was injected intra-articularily into a knee of a subject to relieve the arthritis pain and inflammation.

The composition can be administered alone or optionally in combination with another active ingredient. For example, a corticosteroid, hydrocortisone-17-valerate 0.2% (w/w) was incorporated into a topical composition containing 0.5% (w/w) N—Ac-L-Val-L-Ala-NH2 to rapidly improve chronic eczema lesions. The composition and the other active ingredient can be administered simultaneously or sequentially. Under such cooperative actions, the N-acyldipeptide derivative and the corticosteroid mutually provided synergetic, synergistic, or enhancing effects for the anti-inflammatory actions.

For synergetic, synergistic, additive, enhancing, or other mutually cooperative beneficial effects, a cosmetic, pharmaceutical, or other agent can be incorporated into the composition of the present invention or administered independently at the same time or different time. These agents include but are not limited to hydroxyacids, ketoacids and related compounds; phenyl alpha acyloxyalkanoic acids and derivatives; N-acyl-aldosamines, N-acylamino acids and related N-acyl compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-rosacea agents; anti-seborrheic agents; hair conditioners and hair treatment agents; anti-aging and anti-wrinkle agents; anti-anxiety agents; anti-convulsant agents; anti-depressant agents; antineoplastic agents; sunblock and sunscreen agents; skin lightening agents; depigmenting agents; astringents; cleansing agents; corn, callus and wart removing agents; skin plumping agents; skin volumizing agents; skin firming agents; matrix metalloproteinase (MMP) inhibitors; topical cardiovascular agents; wound-healing agents; gum disease or oral care agents; amino acids; tripeptides; oligopeptides; polypeptides; carbohydrates; aminocarbohydrates; vitamins; corticosteroids; tanning agents; hormones; retinoids; peroxides; peracids; superoxides, ozonides, persulfates, and active agents.

The above agents include, but are not limited to, the following: abacavir, abciximab, abelcet, acamprosate, acarbose, acebutolol, acetaminophen, acetaminosalol, acetazolamide, acetic acid, acetic peracid, acetic peroxide, acetohydroxamic acid, acetylcysteine, acetylsalicylic acid, N-acylglutathione esters, acitretin, aclovate, acrivastine, acthrel, actidose, actigall, actiq, acyclovir, adalimumab, adapalene, adefovir dipivoxil, adenosine, agalsidase, albendazole, albumin, albuterol, alclometasone dipropionate, aldesleukin, alefacept, alemtuzumab, alendronate, alfuzosin, alitretinoin, allantoin, allium, allopurinol, alloxanthine, almotriptan, alosetron, alpha tocpheral, alpha1-proteinase, alprazolam, alprenolol, alprostadil, alteplase, altretamine, aluminum acetate, aluminum chloride, aluminum chlorohydroxide, aluminum hydroxide, amantadine, amifostine, amiloride, aminacrine, amino acid, aminobenzoate, p-aminobenzoic acid, aminocaproic acid, aminohippurate, aminolevulinic acid, aminosalicylic acid, amiodarone, amitriptyline, amlodipine, amocarzine, amodiaquin, amorolfine, amoxapine, amoxicillin, amphetamine, amphotericin, ampicillin, amprenavir, anagrelide, anakinra, anastrozole, anisindione, anthralin, antihemophilic, antithrombin, anti-thymocyte, antivenin, apomorphine, aprepitant, aprotinin, arbutin, argatroban, aripiprazole, ascorbic acid, ascorbyl palmitate, aspirin, atazanavir, atenolol, atomoxetine, atorvastatin, atovaquone, atropine, azathioprine, azelaic acid, azelastine, azithromycin, baclofen, bacitracin, balsalazide, balsam, basiliximab, beclomethasone dipropionate, bemegride, benazepril, bendroflumethiazide, benzocaine, benzoic acid, benzonatate, benzophenone, benzoyl peroxide, benztropine, bepridil, beta carotene, betamethasone dipropionate, betamethasone valerate, betaxolol, bethanechol, bevacizumab, bexarotene, bicalutamide, bimatoprost, bioflavonoids, biotin, biperiden, bisacodyl, bisoprolol, bivalirudin, bortezomib, bosentan, botulinum, brimonidine, brinzolamide, bromocriptine, brompheniramine, budesonide, bumetanide, bupivacaine, buprenorphine, bupropion, burimamide, buspirone, busulfan, butabarbital, butalbital, butenafine, butoconazole, butorphanol, butyl aminobenzoate, cabergoline, caffeic acid, caffeine, calcipotriene, calcitonin-salmon, calcitriol, calcium peroxide, calfactant, *Camellia sinensis*, camphor, candesartan cilexetil, capecitabine, capreomycin, capsaicin, captopril, carbamazepine, carbamide peroxide, carbidopa, carbinoxamine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, coal tar, coal tar extracts (LCD), codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, efalizumab, eflornithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, etidocaine, etomidate, famciclovir, famotidine, felodipine, fentanyl, ferulic acid, fexofenadine, flecainide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glutathione, glycolic acid, griseofulvin, guaifenesin, guanethidine, N-guanylhistamine, haloperidol, haloprogin, hexylresorcinol, homatropine, homosalate, hormone, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, niacin, niacinamide, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, peptide, perazine, pergolide, perindopril, permethrin, phencyclidine, phenelzine, pheniramine, phenmetrazine, phenobarbital, phenol, phenoxybenzamine, phentolamine, phenylephrine, phenylpropanolamine, phenytoin, physostigmine, pilocarpine, pimecrolimus, pimozide, pindolol, pioglitazone, pipamazine, piperonyl butoxide, pirenzepine, podofilox, podophyllin, potassium peroxide, povidone iodine, pramipexole, pramoxine, prazosin, prednisone, prenalterol, prilocaine, procainamide, procaine, procarbazine, promazine, promethazine, promethazine propionate, propafenone, propoxyphene, propranolol, propylthiouracil, protein, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis-retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thiethylperazine, thioctic acid (lipoic acid), thioridazine, thiothixene, thymol, tiagabine, timolol, tinidazole, tioconazole, tirofiban, tizanidine, tobramycin, tocainide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, valacyclovir, vardenafil, venlafaxine, verapamil, vitamin, vitamin E acetate, voriconazole, warfarin, wood tar, xanthine, zafirlukast, zaleplon, zinc pyrithione, ziprasidone, zolmitriptan and zolpidem.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Example 1

In one of the studies related to skin changes associated with aging, skin thickness was measured by micrometer calipers as follows.

The skin was grasped with a 2×6 cm metal hinge; the internal faces of which were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of two whole-skin layers. Triplicate measurements on treated sites were done and an average number was used for calculation of the skin thickness.

In other studies, test sites of skin 17 mm in diameter were used, the circular sites were marked with permanent ink. Intervening control sites were also 17 mm in diameter. Thickness of skin of all sites was measured directly by means of an electronic digital caliper. In this instance the jaws of the caliper were opened to 17 mm, applied with pressure to the skin sites and then closed to firm tightness. Thickness of skin was then read off the screen of the calipers. Measurements of all sites were made in triplicates.

Example 2

A typical oil-in-water emulsion or cream composition containing a bioactive dipeptide derivative of the present invention was formulated as follows.

A bioactive dipeptide derivative of the present invention 0.2 g was dissolved in 39.8 ml warm solution prepared from 80 parts water and 20 parts propylene glycol by volume (hereinafter referred to as WP82). The solution or suspension thus obtained was mixed with 60 g oil-in-water emulsion or cream. The oil-in-water emulsion or cream thus formulated contained 0.2% bioactive dipeptide derivative of the present invention in oil-in-water emulsion or cream. Under similar conditions, emulsion or cream compositions containing 0.01% to 10% bioactive dipeptide derivative of the present invention were formulated.

As an illustration, N—Ac-L-Val-L-Ala-NH2 powder 0.2 g was dissolved in 39.8 ml warm WP82 solution. The clear solution thus obtained was mixed with 60 g oil-in-water emulsion or cream. The oil-in-water emulsion or cream thus formulated contained 0.2% N—Ac-L-Val-L-Ala-NH$_2$. Under the similar conditions, the following emulsion or cream compositions were formulated:
N—Ac-L-Ile-L-Ala-NH$_2$ 1% (w/w) emulsion or cream;
N—Ac-L-Leu-L-Ala-NH$_2$ 1% (w/w) and 5% (w/w) emulsions or creams.
N—Ac-L-Val-L-Ala-NH$_2$ 0.01%, 0.05%, 0.1%, 0.2%, 0.3%, 0.4%, 0.5%, 1% and 2%, all by weight,
emulsions or creams.

Vehicle control emulsion or cream composition was prepared in the same manner except that the bioactive dipeptide derivative of the present invention was replaced by water.

Example 3

As another illustration to Example 2, 5 g N—Ac-L-Leu-Gly-NH2 powder was dissolved in 35 ml warm WP82 solution. The clear solution thus obtained was mixed with 60 g oil-in-water emulsion or cream. The oil-in-water emulsion or cream thus formulated contained 5% (w/w) N—Ac-L-Leu-Gly-NH2.

Under the similar conditions, the following emulsion or cream compositions were formulated, all percentages are by weight:
N—Ac-β-Ala-Gly-NH$_2$ 1% in emulsion or cream
N—Ac-L-Asn-Gly-NH$_2$ 4% in emulsion or cream
N—Ac-Abz-Gly-NH$_2$ 5% in emulsion or cream N—Ac-L-Cys-Gly-NH$_2$ 10% in emulsion or cream
N—Ac-Gaba-Gly-NH$_2$ 8% in emulsion or cream
N—Ac-Gly-Gly-NH$_2$ 5% in emulsion or cream
N—Ac-L-His-Gly-NH$_2$ 5% in emulsion or cream
N—Ac-L-Ile-Gly-NH$_2$ 0.5%, 1%, 2%, 5%, 6%, and 10% in emulsions or creams
N—Ac-L-Leu-Gly-NH$_2$ 5%, 6%, 7%, 8% and 10% emulsions or creams
N—Ac-L-Pro-Gly-NH$_2$ 3% in emulsion or cream
N—Ac-L-Ser-Gly-NH$_2$ 5% in emulsion or cream
N—Z-L-Tyr-Gly-NH$_2$ 5% in emulsion or cream
N—Ac-L-Val-Gly-NH$_2$ 5% and 10% in emulsions or creams Example 4

As another illustration to Example 2, and under the similar conditions, the following emulsion or cream compositions were also formulated, all percentages are by weight:
N—Ac-βAla-L-His-NH$_2$ 5% in emulsion or cream
N,N'-diAc-βAla-His-NH$_2$ 5% in emulsion or cream
N—Ac-βAla-L-His-OH 5% in emulsion or cream
N—Ac-βAla-L-His-OEt 5% in emulsion or cream
N—Ac-L-Ala-L-Ile-NH$_2$ 1% in emulsion or cream
N—Ac-L-Ile-L-Ile-NH$_2$ 1% in emulsion or cream
N—Ac-L-Leu-L-Leu-NH$_2$ 1% in emulsion or cream
N—Ac-L-Ile-L-Tyr-NH$_2$ 1% in emulsion or cream
N—Ac-L-Leu-L-Tyr-NH$_2$ 1% in emulsion or cream
N—Ac-L-Tyr-L-Tyr-NH$_2$ 1% in emulsion or cream
N—Ac-L-Val-L-Tyr-NH$_2$ 5% in emulsion or cream
N—Ac-L-Tyr-L-Tyr-OH 1% in emulsion or cream
N—Ac-L-Tyr-L-Tyr-OEt 1% in emulsion or cream
N—Ac-L-Tyr-L-Tyr-NHNH$_2$ 0.6% in emulsion or cream
N—Ac-L-Tyr-L-Tyr-NHNHAc 0.7% in emulsion or cream Example 5

A typical solution composition containing a bioactive dipeptide derivative of the present invention was formulated as follows.

A bioactive dipeptide derivative of the present invention, 0.1 g, was dissolved in 99.9 ml solution prepared from 40 parts water, 40 parts ethanol and 20 parts propylene glycol by volume (hereinafter referred to as WEP442). The solution thus formulated contained 0.1% (w/w) bioactive dipeptide derivative of the present invention in solution composition. Under similar conditions, solution compositions containing 0.01% to 10%, by weight, bioactive dipeptide derivative of the present invention were formulated.

As an illustration, N—Ac-L-Val-L-Ala-NH2 powder, 0.1 g, was dissolved in 99.9 ml WEP442. The solution composition thus formulated had pH 5.4, and contained 0.1% (w/w) N—Ac-L-Val-L-Ala-NH2.

Under the similar conditions, solution compositions were formulated as follows, wherein all percentages are by weight:
N—Ac-L-Val-L-Ala-NH$_2$: 0.01%, pH 4.7; 0.05%, pH 5.0; 0.1%, pH 5.4; 0.2%, pH 5.6; 0.4%, pH 5.8; 0.5%, pH 5.9; all in WEP442
N—Ac-L-Ile-L-Ala-OH: 0.4% in WEP442, pH 3.9
N—Ac-L-Leu-L-Ala-OH: 0.4% in WEP442
N—Ac-L-Val-L-Ala-OH: 0.4% in WEP442, pH 3.0
N—Pr-L-Val-L-Ala-OH: 0.4% in WEP442, pH 3.7
N—Ac-L-Cys-L-Cys-NH$_2$: 0.4% in WEP 442
N—Ac-L-Cys-L-Cys-OH: 0.5% in WEP 442, pH 5.3
N—Ac-L-Ile-Gly-OH: 0.4% in WEP442, pH 3.2
N—Ac-L-Cys-Gly-NH$_2$: 1% in WEP442, pH 6.4
N—Ac-L-Leu-Gly-NH$_2$: 1%, pH 5.3; 2.5%, pH 5.4; 5%, pH 5.4; 10% pH 5.4; all in WEP442.
N—Ac-L-Leu-Gly-OH: 0.4% in WEP442, pH 3.8
N—Pr-L-Leu-Gly-OH: 0.4% in WEP442, pH 3.5
N—Ac-L-Pro-Gly-OH: 5% in 90 parts water and 10 parts propylene glycol by volume (WP91), pH 6.6
N—Ac-L-Tyr-Gly-NH$_2$: 2.5% in WEP442
N—Ac-L-Gln-Gly-NH$_2$: 2.5% in WEP442
N—Ac-L-Val-Gly-OH: 0.4% in WEP442, pH 3.2
N—Ac-Gly-L-Pro-NH$_2$: 5% in WEP442
βAla-L-His-NH$_2$: 5% in WEP442, pH 6.5
N, N'-DiAc-βAla-L-His-NH$_2$: 3% in WEP442, pH 7.0; 4% in WP82, pH 7.1
N—Ac-Gaba-Gly-NH$_2$: 5% in WEP442, pH 5.8
N—Ac-βAla-Gly-NH$_2$: 5% in WEP442, pH 5.2
N—Ac-Gly-L-Pro-NH$_2$: 5% in WEP442
N—Ac-L-Cys-L-Tyr-NH$_2$: 1% in WEP442, pH 6.4
N—Ac-L-Tyr-L-Tyr-OEt: 1% in a solution prepared from 80 parts ethanol and 20 parts propylene glycol by volume (hereinafter referred to as EP82)
N—Ac-L-Tyr-L-Tyr-NH$_2$: 0.5%, 1% in EP82; 0.5%, 3% in WEP442, pH 6.7
N—Ac-L-Tyr-L-Tyr-OH: 0.3%, 0.4%, 0.5%, or 1% in WEP442, all pH 3.7
N—Ac-L-Tyr-L-Tyr-NHNH$_2$: 0.3% in WEP442, pH 5.8; 2% in WEP442
N—Ac-L-Tyr-L-Tyr-NHNHAc: 0.3% and 0.5% in WEP442, pH 5.5; 3% in WEP442
N—Ac-L-Phe-L-Phe-NH$_2$: 0.4% in WEP442
N—Ac-L-Trp-L-Trp-NH$_2$: 0.4% in WEP442

Vehicle control compositions such as WEP442 and EP82 were prepared in the same manner but without any bioactive dipeptide derivative of the present invention.

Example 6

A female subject, age 41, topically applied twice daily N—Ac-L-Tyr-L-Tyr-NH2 3% (w/v) in WEP442, pH 6.7 as prepared in Example 5, to her left forearm, and a vehicle control WEP442 to her right forearm for three weeks. After 3 weeks, while there was no change in skin thickness of her right forearm, her left forearm had increased 14% in skin thickness as measured by the micrometer calipers as shown in Example 1. After 4 weeks her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 17% in skin thickness as measured by the micrometer calipers. This result indicates that N—Ac-L-Tyr-L-Tyr-NH$_2$ has the potential of providing therapeutic effects for topical treatment of disturbed keratinization and aging related changes of skin, nail and hair.

Example 7

A female subject, age 52, topically applied twice daily N—Ac-L-Tyr-L-Tyr-NH2 3% (w/v) in WEP442, pH 6.7 as prepared in Example 5, to her left forearm, and a vehicle control WEP442 to her right forearm for two weeks. After two weeks her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 13% in skin thickness as measured by the micrometer calipers as shown in Example 1. This result shows that N—Ac-L-Tyr-L-Tyr- NH2 has the potential of providing therapeutic effects for topical treatment of disturbed keratinization and aging related changes of skin, nail and hair.

Example 8

A female subject, age 51, topically applied twice daily 2% (w/v) N—Ac-L-Tyr-L-Tyr-NHNH$_2$ in WEP442 as prepared in Example 5, to her left forearm, and a vehicle control WEP442 to her right forearm for three weeks. After one week while there was no change in skin thickness of her right forearm, her left forearm had increased 15% in skin thickness as measured by the micrometer calipers as shown in Example 1. After three weeks her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 32% in skin thickness as measured by the micrometer calipers. This result indicates that N—Ac-L-Tyr-L-Tyr-NHNH$_2$ has the potential of providing therapeutic effects for topical treatment of disturbed keratinization and aging related changes of skin, nail and hair.

Example 9

A female subject, age 52, topically applied twice daily 2% (w/v) N—Ac-L-Tyr-L-Tyr-NHNH2 in WEP442 as prepared in Example 5, to her left forearm, and a vehicle control WEP442 to her right forearm for two weeks. After two weeks her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 14% in skin thickness as measured by the micrometer calipers as shown in Example 1. This result indicates that N—Ac-L-Tyr-L-Tyr-NHNH$_2$ has the potential for topical treatment of disturbed keratinization and aging related changes of skin, nail and hair.

Example 10

A female subject, age 51, topically applied twice daily 3% (w/v) N—Ac-L-Tyr-L-Tyr-NHNHAc in WEP442 as prepared in Example 5, to her left forearm, and a vehicle control WEP442 to her right forearm for three weeks. After one week while there was no change in skin thickness of her right forearm, her left forearm had increased 21% in skin thickness as measured by the micrometer calipers as shown in Example 1. After three weeks her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 32% in skin thickness as measured by the micrometer calipers. This result shows that N—Ac-L-Tyr-L-Tyr-NHNHAc has the potential of providing therapeutic effects for topical treatment of disturbed keratinization and aging related changes of skin, nail and hair.

Example 11

A female subject, age 73, topically applied twice daily 3% (w/v) N—Ac-L-Tyr-L-Tyr-NH2 in WEP442 as prepared in Example 5, to her left forearm, and a vehicle control WEP442 to her right forearm for 4 weeks. After 2 weeks, there was no change in skin thickness of her right forearm, her left forearm had increased 19% in skin thickness as measured by the micrometer calipers as shown in Example 1. At the end of 4 weeks, her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 21% in skin thickness as measured by the micrometer calipers. This result indicates that N—Ac-L-Tyr-L-Tyr-NH2 has the potential of providing therapeutic effects for topical treatment of disturbed keratinization and aging related changes of skin, nail and hair.

Example 12

A male subject, age 79, having intensive itch and erythema on his left arm from insect bites, topically applied 10% (w/w) N—Ac-L-Leu-Gly-NH$_2$ cream as formulated in Example 3 on the involved lesions. The itch stopped within a few minutes, and the pruritus did not return for the next 6 hours. The erythema and inflammation also improved after 12 hours. The result shows that N—Ac-L-Leu-Gly-NH$_2$ has the potential of providing therapeutic effects for topical treatment of symptoms or syndromes associated with nerve disorders and inflammation.

Example 13

A male subject, age 80, having chronic inflammation, erythema, eczema with thick scales and itch on his right leg for more than 10 years, failed to respond with conventional treatments including topical corticosteroids. The involved skin was divided into two lesions for testing. The subject topically applied twice daily to one lesion 0.5% (w/v) N—Ac-L-Tyr-L-Tyr-NH$_2$ solution composition, pH 6.7 prepared from 4 parts water, 76 parts ethanol and 20 parts propylene glycol by volume, and to second lesion 0.4% (w/v) N—Ac-L-Val-L-Ala-NH$_2$ in WEP442 solution composition, pH 5.8 as shown in Example 5. The itch stopped within a few minutes, and the thick scales of both lesions started to disappear in the next few days. At the end of 4 weeks, the erythema and thick scales of both lesions disappeared almost completely and the treated skin sites were smooth, soft, even-toned, brighter and more elastic when the skin was stretched. The treated skin appeared much lighter in skin color as compared to the surrounding untreated skin site. The treated skin had 95-100% improvement as judged by clinical evaluation. The result shows that both N—Ac-L-Tyr-L-Tyr-NH$_2$ and N—Ac-L-Val-L-Ala-NH$_2$ have the potential of providing therapeutic effects for topical treatment of symptoms or syndromes associated with nerve disorders, disturbed keratinization, aging skin, wrinkles, age spots, hyperpigmentation, inflammation, deranged immune system, and for skin lightening.

Example 14

A female subject, age 87, having chronic inflammation, dermatitis, or eczema with thick scales and itch on her right leg for more than 7 years, failed to respond with conventional treatments including topical corticosteroids. The subject topically applied twice daily 10% (w/w) N—Ac-L-Leu-Gly-NH2 cream as formulated in Example 3 on the involved lesions. The itch stopped within a few minutes, and the thick scales started to disappear in the next few days. At the end of one week, the treated skin had 50% improvement as judged by clinical evaluation. The result shows that N—Ac-L-Leu-Gly-NH2 has the potential of providing therapeutic effects for topical treatment of symptoms or syndromes associated with nerve disorders, disturbed keratinization, inflammation and deranged immune system.

Example 15

A female subject, age 50, having chronic inflammation, dermatitis, or eczema with scales, erythema and itch for more than 15 years, failed to respond with conventional treatments including topical corticosteroids. The subject topically applied twice daily 7% (w/w) N—Ac-L-Leu-Gly-$NH_2$ oil-in-water emulsion as formulated in Example 3 on the involved lesions. The itch stopped within a few minutes, and the lesions improved for the next few days. At the end of 10 days, the scales and erythema disappeared almost completely and the treated skin had 90-100% improvement as judged by clinical evaluation. The result shows that N—Ac-L-Leu-Gly-$NH_2$ has the potential for topical treatment of symptoms or syndromes associated with nerve disorders, disturbed keratinization, inflammation and deranged immune system.

Example 16

A female subject, age 43, having chronic inflammation, dermatitis, or eczema with scales, erythema and itch covering large areas of the body for many years, failed to respond with conventional treatments including topical corticosteroids. The subject topically applied twice daily on the involved lesions 6% (w/w) N—Ac-L-Leu-Gly-NH2 oil-in-water emulsion as formulated in Example 3. The itch stopped within a few minutes, and the lesions improved for the next few days. At the end of 10 days, the scales and erythema disappeared almost completely and the treated skin had 95% improvement as judged by clinical evaluation. The result shows that N—Ac-L-Leu-Gly-NH2 has the potential for topical treatment of symptoms or syndromes associated with nerve disorders, disturbed keratinization, inflammation and deranged immune system.

Example 17

A male subject, age 80, having chronic inflammation and eczema with thick scales and itch on his legs, failed to respond with conventional treatments including topical corticosteroids. The subject topically applied twice daily to one leg 2% (w/v) N—Ac-L-Val-L-Ala-$NH_2$ cream as formulated in Example 2, and to another leg 0.5% (w/w) N—Ac-L-Tyr-L-Tyr-NHNHAc in WEP442, pH 5.5 as formulated in Example 5, on the involved lesions. For both treated legs, the itch stopped within a few minutes, and the thick scales started to disappear in the next few days. The eczema lesions also improved substantially over the next few weeks, and the skin became soft and smooth. At the end of four weeks, the treated legs had 95-100% improvement as judged by clinical evaluations. The results show that the dipeptide derivatives of the present invention have the potential for topical treatment of symptoms or syndromes associated with nerve disorders, disturbed keratinization, inflammation and deranged immune system.

Example 18

A male subject, age 79, developed skin allergy from eating shellfish with intensive itch and reddish papules on his back and thighs that failed to respond with conventional treatments including topical corticosteroids. The subject topically applied twice daily 0.5% (w/w) N—Ac-L-Val-L-Ala-$NH_2$ cream as formulated in Example 2 on the involved lesions. The itch stopped within a few minutes, and the reddish papules started to disappear in the next few days. At the end of 5 days, the treated skin had 75% improvement as judged by clinical evaluation. The result shows that N—Ac-L-Val-L-Ala-$NH_2$ has the potential for topical treatment of symptoms or syndromes associated with nerve disorders, inflammation and deranged immune system.

Example 19

A male subject, age 80, having inflammatory dermatitis on both arms with erythema and intensive itch and failed to respond with conventional treatments including topical corticosteroids. The subject topically applied twice daily 0.4% (w/v) N—Ac-L-Tyr-L-Tyr-OH in WEP442, pH 3.7 as formulated in Example 5 on the involved lesions. The itch stopped within a few minutes, and the erythema started to disappear in the next few days. At the end of one week, the treated skin had 95% improvement as judged by clinical evaluation. The result shows that N—Ac-L-Tyr-L-Tyr-OH has the potential for topical treatment of symptoms or syndromes associated with nerve disorders and inflammation.

Example 20

A male subject, age 80, having chronic eczema with intensive itch, failed to respond with conventional treatments including topical corticosteroids. The subject took 1 mg N—Ac-L-Tyr-L-Tyr-OH powder under the tongue until it was dissolved completely. The same dose was taken twice daily for the next three days. Systemic administration of N—Ac-L-Tyr-L-Tyr-OH under the tongue did not provoke any irritation or side reactions. Such systemic administration of the bioactive dipeptide derivative of the present invention is believed to have the potential of treating diseases, symptoms or syndromes associated with immune, tumors, cancers, nervous, vascular, musculoskeletal, cutaneous system, or other tissues and systems.

Example 21

A typical in vitro screen for anti-inflammatory effects was carried out as follows.

THP-1 leukemia cells (monocytic leukemic human cell line) were cultured and either untreated or treated with a bioactive dipeptide derivative (100 µg/ml) of the present invention for 24 hours. The untreated or treated leukemia cells were then treated with angiocidin (10 µg/ml) for 24 hours to induce interleukin-6 (IL-6) which was an indicator of the inflammation. The induced IL-6 was measured quantitatively by ELISA (enzyme-linked immunosorbent assay). The test results showed that N—Ac-L-Val-L-Ala-NH2 inhibited the production of IL-6 by approximately 70%. Therefore, the bioactive dipeptide derivatives of the present invention, such as N—Ac-L-Val-L-Ala-NH2, have the potential use as nonsteroidal anti-inflammatory substances.

Example 22

In one embodiment, a composition containing a bioactive dipeptide derivative of the present invention for systemic administration can be prepared as follows.

For injection administration, a composition can be prepared with or without a thickening agent, such as methyl cellulose. Methyl cellulose 1% (w/v) in water solution was prepared by adding 1 g methyl cellulose in 90 ml water, and the mixture was gently homogenized. More water was added to make the final volume of 100 ml. The vehicle composition thus prepared contained 1% (w/v) methyl cellulose as a thickener. N—Ac-L-Tyr-L-Tyr-NH2, 100 mg, was dissolved in 5 ml water with or without 1% (w/v) methyl cellulose, and the solutions in injection vials were sterilized at 1000 C for 30 minutes. The compositions thus obtained contained 2% (w/v) or 20 mg/ml N—Ac-L-Tyr-L-Tyr-NH2 suitable for intra-articular, intralesional, or subcutaneous injection, or other systemic administration.

Under the same conditions, the following compositions for systemic administration were prepared, all percentages are by weight: 2% or 20 mg/ml N—Ac-L-Tyr-L-Tyr-NHNH2 in water with or without 1% methyl cellulose; 2% or 20 mg/ml N—Ac-L-Tyr-L-Tyr-NHNHAc in water with or without 1% methyl cellulose; 0.2% or 2 mg/ml N—Ac-L-Val-L-Ala-NH2 in water with or without 1% methyl cellulose; and 0.2% or 2 mg/ml N—Ac-L-Tyr-L-Tyr-OH in water with or without 1% methyl cellulose.

Example 23

Bioactive dipeptide derivative of the present invention as potential treatment of knee osteoarthritis by intra-articular injections.

A male subject, age 90, had severe osteoarthritis of both knees for four and half years. Prior therapy had included intra-articular injections of corticosteroids and hyaluronic acid as well as celecoxib (Celebrex) orally (200 mg) twice daily. Such therapy had provided only mild transitory relief of knee pain and edema, and edema of lower legs.

Intra-articular injections of 0.2% (w/v) N—Ac-L-Val-L-Ala-NH2 in water, 1 ml (2 mg) as prepared in Example 22 were administered to each knee. The pains in both knees disappeared 10-15 minutes after the injections, and the relief of pains lasted for 24 hours. Edema and inflammation of the knees and lower legs had diminished for approximately the same 24 hour period. Repeat injections of the same composition were administered once a week for five weeks to provide continued relief of pain, edema and inflammation.

In another trial, intra-articular injections of 0.2% (w/v) N—Ac-L-Val-L-Ala-NH2 with 1% (w/v) methyl cellulose in water, 0.4 ml (0.8 mg) as prepared in Example 22 were also administered to each knee at different times. The pains in both knees disappeared 10-15 minutes after the injections, and the relief of pains lasted for 24 hours. Edema and inflammation of the knees and lower legs had diminished for approximately the same 24 hour period.

The above results show that N-acyldipeptide derivatives of the present invention have the potential of treating inflammation, arthritis, pain, other immune and nerve disorders via systemic administration.

Example 24

A typical combination composition for synergetic, synergistic or additive effects was prepared as follows.

N—Ac-L-Val-L-Ala-NH2 400 mg and N-acetyl-D-glucosamine (NAG) 400 mg were dissolved in 90 ml solution prepared from water 40 parts, ethanol 40 parts and propylene glycol 20 parts by volume (WEP442), and the final volume was made up to 100 ml. The composition thus prepared had pH 5.6, and contained 0.4% (w/v) N—Ac-L-Val-L-Ala-NH2 and 0.4% (w/v) NAG.

A female subject, age 41, had inflammatory lesions on her left arm with intensive itch and reddish papules that failed to respond with conventional treatments including topical corticosteroids. The subject topically applied twice daily the above combination composition containing 0.4% N—Ac-L-Val-L-Ala-NH2 and 0.4% NAG on the involved lesions. The itch stopped within a few minutes, and the reddish papules started to disappear in the next few days. At the end of 5 days, the treated skin had more than 90% improvement as judged by clinical evaluation. The treated skin sites showed that the skin was smooth and soft to touch and appearance. The result shows that the combination of N—Ac-L-Val-L-Ala-NH2 and NAG has synergetic or synergistic effects, and can improve the lesions faster than the non-combination composition. It is believed that the combination composition has the potential for topical treatment of symptoms or syndromes associated with disturbed keratinization, nerve disorders, inflammation and deranged immune system.

Example 25

As an another illustration, N—Ac-L-Tyr-L-Tyr-NH2, 500 mg, and hydrocortisone-17-valerate, 200 mg, were dissolved in 90 ml solution prepared from 80 parts ethanol and 20 parts propylene glycol by volume (EP82), and the final volume was made up to 100 ml. The composition thus prepared contained 0.5% (w/v) N—Ac-L-Tyr-L-Tyr-NH$_2$ and 0.2% (w/v) hydrocortisone-17-valerate.

A male subject, age 80, had chronic eczema on his right leg with intensive itch and thick scales, which failed to respond with conventional treatments including topical corticosteroids. The subject topically applied twice daily the above combination composition containing 0.5% (w/v) N—Ac-L-Tyr-L-Tyr-NH2 and 0.2% (w/v) hydrocortisone-17-valerate on the involved lesions. The itch stopped within a few minutes, and the thick scales started to disappear in the next few days. At the end of 7 days, the treated skin had 80% improvement as judged by clinical evaluation. The treated skin sites showed that the skin was smooth and soft to the touch and appearance. The result shows that the combination of N—Ac-L-Tyr-L-Tyr-NH2 and hydrocortisone-17-valerate has synergetic or synergistic effects, and can improve the lesions much faster than the non-combination composition. Thus, the combination composition has the potential for topical treatment of symptoms or syndromes associated with disturbed keratinization, nerve disorders, inflammation and deranged immune system.

Example 26

A male subject, age 41, had inflammatory eczema on his left hand with itch, erythema and some scales for 6 months, which failed to respond with conventional treatments including topical corticosteroids. The subject topically applied twice daily the combination composition containing 0.5% (w/v) N—Ac-L-Tyr-L-Tyr-NH2 and 0.2% (w/v) hydrocortisone-17-valerate as described in Example 25 on the involved lesions. The itch stopped within a few minutes, and the erythema and scales started to disappear in the next few days. At the end of 5 days, the treated skin had 75% improvement as judged by clinical evaluation. The treated skin sites showed that the skin was smooth and soft to the touch and appearance. The result shows that the combination of N—Ac-L-Tyr-L-Tyr-NH2 and hydrocortisone-17-valerate has synergetic or synergistic effects, and can improve the lesions much faster than the non-combination composition. Thus, the combination composition has the potential for topical treatment of symptoms or syndromes associated with disturbed keratinization, nerve disorders, inflammation and deranged immune system.

Example 27

A typical example of a topical administration for systemic therapeutic effects was carried out as follows. A male subject, age 80, having sprained his left leg near the knee with inflammation for several weeks had severe pain each time walking. Massage therapy and conventional treatments provided only a temporary relief. The subject topically applied and rubbed 0.4% (w/v) N—Ac-L-Val-L-Ala-NH2 in WEP442, pH 5.8 as prepared in Example 5 onto the left thigh and calf sites of skin for 30 seconds at night. The next morning, the subject was surprised to discover that he could walk slowly without feeling any pain on his left leg. The inflammation in his left leg also subsided significantly. The clinical evaluation showed that he had approximately 75% improvement on his left leg.

The above result shows that topical administration of a bioactive dipeptide derivative of the present invention has the potential of providing therapeutic effects for pain, inflammation and arthritis.

Example 28

A male subject, age 80, had a skin cut with an open wound about 2 cm long and a feeling of moderate pain on his left leg. The subject topically applied twice daily 0.5% (w/w) N—Ac-L-Val-L-Ala-NH2 cream as formulated in Example 2 on the wound. The pain stopped within a few minutes, and the wound started to heal in the next few days. At the end of 5 days, the wound had healed nearly completely, and treated skin appeared normal without any signs of scar formation. The wound had 95-100% improvement as judged by clinical evaluation. The result shows that N—Ac-L-Val-L-Ala-NH2 has the potential for topical treatment of skin wounds.

Example 29

Stretch marks, known as striae, are visible linear scars caused by changes in collagen fibers and over stretching of the skin. Stretch marks are quite common in most adult women, and they readily develop at puberty or during pregnancy. They are also very common in obese people with sudden loss of weight. At present, there is no cure or effective treatment.

A male subject, age 41, having lost a total of about 60 pounds from overweight over the last 10 years, developed multiple lesions of stretch marks over the body. The subject selected two separate lesions of stretch marks, and topically applied twice daily 0.5% (w/w) N—Ac-L-Val-L-Ala-NH2 cream (Example 2) on one lesion and 0.5% (w/v) N—Ac-L-Tyr-L-Tyr-NH2 solution in WEP442, pH 6.7 (Example 5) on the other lesion with untreated lesions of stretch marks as a control.

In contrast to untreated lesions, the treated lesions of stretch marks slowly improved over the next few weeks. At the end of four weeks, the fine lines of stretch marks started to disappear, and deeper lines became less deep. The treated lesions had approximately 25% improvement as judged by clinical evaluation.

The above results show that a bioactive dipeptide derivative of the present invention has the potential of providing therapeutic effects via topical administration to treat stretch marks, skin atrophy, skin scars, skin thinning, and other skin defects caused by changes to dermal components including collagen and elastic fibers.

Example 30

A male subject, age 42, had multiple lesions of insect bites (mosquitoes) over the face and arms with itch and inflammatory lesions of more than 1 cm in size. For testing purposes, the subject divided the lesions into three groups: the first group was treated with vehicle control, the second and third groups were treated with active compositions. The subject topically applied twice daily 0.5% (w/v) N—Ac-L-Val-L-Ala-NH$_2$ solution in WEP442, pH 5.9 on the lesions of the second group, and 0.5% (w/v) N—Ac-L-Tyr-L-Tyr-NH$_2$ solution in WEP442, pH 6.7 (Example 5) on the lesions of the third group. While there was no immediate effect in the lesions treated with vehicle control in the first group, the itch stopped completely within a few minutes of topical applications in the second and third groups. The lesions in the second and third groups also started to improve over the next few days. At the end of three days, while there was no discernible change in the lesions treated with vehicle control in the first group, the lesions in the second and third groups had 90-100% improvement with nearly complete disappearance of inflammatory lesions.

The above results show that bioactive dipeptide derivatives of the present invention have the potential of providing therapeutic effects via topical administration to treat insect bites, inflammation, pain, other immune and nerve disorders.

Example 31

A male subject, age 42, having a sprained right shoulder with inflammation and pain caused by heavy lifting 6 weeks earlier did not respond to conventional treatments. The subject topically applied twice daily 0.5% (w/v) N—Ac-L-Tyr-L-Tyr-NH2 in WEP442 solution, pH 6.7 as prepared in Example 5. After three days of topical application, the pain disappeared completely and the inflammation diminished substantially. At the end of 5 days, the right shoulder had 90% improvement as determined by clinical evaluation. The result shows that the bioactive dipeptide derivative of the present invention has the potential for treating pain and inflammation of joints by topical administration.

Example 32

A male subject, age 41, having muscle pain in both arms with inflammation caused by heavy lifting several weeks earlier did not improve with the conventional treatments. The subject topically applied twice daily 0.5% (w/v) N—Ac-L-Val-L-Ala-NH2 in WEP442 solution, pH 6.7 as prepared in Example 5 to the affected area of skin. The pain diminished with less inflammation over the next day. At the end of five days, the pain and inflammation disappeared completely, and the arms had 95%-100% improvement as determined by clinical evaluation.

The result shows that the bioactive dipeptide derivative of the present invention has the potential of treating pain and inflammation of muscles by topical administration.

Example 33

A female subject, age 52, had multiple lesions of chigger bites (grass mites) over the legs with intensive itch and red inflammatory lesions. The subject topically applied twice daily 0.5% (w/v) N—Ac-L-Val-L-Ala-NH₂ solution in WEP442, pH 6.7 (Example 5) on the lesions. The itch stopped within a few minutes after the topical application, and the red inflammatory lesions started to clear over the next few days. At the end of five days, all red and inflammatory lesions disappeared completely, and the treated skin appeared normal. The lesions on the legs had 100% improvement as judged by clinical evaluation.

The above result shows that bioactive dipeptide derivatives of the present invention have the potential of providing therapeutic effects via topical administration to treat insect bites, inflammation, pain, other immune and nerve disorders.

Example 34

A female subject, age 73, topically applied twice daily 1% (w/v) N—Ac-L-Tyr-L-Tyr-OH in WEP442 as prepared in Example 5, to her left forearm, and a vehicle control WEP442 to her right forearm for 4 weeks. After 2 weeks, there was no change in skin thickness of her right forearm, her left forearm had increased 16% in skin thickness as measured by the micrometer calipers as shown in Example 1. At the end of 4 weeks, her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 17% in skin thickness as measured by the micrometer calipers. This result indicates that N—Ac-L-Tyr-L-Tyr-OH has the potential for topical treatment of disturbed keratinization and aging related changes of skin, nail and hair.

Example 35

A female subject, age 41, topically applied twice daily 3% (w/v) N—Ac-L-Tyr-L-Tyr-NHNHAc in WEP442 as prepared in Example 5, to her left forearm, and a vehicle control WEP442 to her right forearm for 6 weeks. After 2 weeks, there was no change in skin thickness of her right forearm, and her left forearm had increased 7% in skin thickness as measured by the micrometer calipers as shown in Example 1. At the end of 6 weeks, her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 23% in skin thickness as measured by the micrometer calipers. This result indicates that N—Ac-L-Tyr-L-Tyr-OH has the potential for topical treatment of disturbed keratinization and aging related changes of skin, nail and hair.

Example 36

A female subject, age 41, topically applied twice daily N—Ac-L-Tyr-L-Tyr-OH 1% (w/v) in WEP442 as prepared in Example 5, to her left forearm, and a vehicle control WEP442 to her right forearm for one week. At the end of one week, her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 16% in skin thickness as measured by the micrometer calipers as shown in Example 1. This result indicates that N—Ac-L-Tyr-L-Tyr-OH has the potential for topical treatment of disturbed keratinization and aging related changes of skin, nail and hair.

Example 37

A female subject, age 59, topically applied twice daily 3% (w/v) N—Ac-L-Tyr-L-Tyr-NH2 in WEP442, pH 6.7 as prepared in Example 5, to her left forearm, and a vehicle control WEP442 to her right forearm for 4 weeks. At the end of 4 weeks, her vehicle treated right forearm was still loose, relatively thin and wrinkled when lifted. In contrast, her left forearm was more firm, smooth, plump, and less wrinkled when lifted. While there was no change in skin thickness of her right forearm, her left forearm had increased 21% in skin thickness as measured by the micrometer calipers as shown in Example 1. This result indicates that N—Ac-L-Tyr-L-Tyr-NH2 has the potential for topical treatment of disturbed keratinization and aging related changes of skin, nail and hair.

Example 38

A male subject, age 80, had multiple varicose veins in his right lower leg for many years resistant to any kind of topical treatments including high potency alpha-hydroxyacids. The lesions of varicose veins covered an area of skin measuring 5 cm×10 cm and appeared more prominent with advancing age. The subject topically applied twice daily 0.5% (w/v) N—Ac-L-Tyr-L-Tyr-NH₂ in WEP442 solution as prepared in Example 5. At the end of four weeks, the lesions of varicose veins appeared less prominent. It is believed that continued topical application will eradicate the varicose veins. This result indicates that N—Ac-L-Tyr-L-Tyr-NH₂ has the potential for topical treatment of varicose veins.

Example 39

A male subject, age 41, performed pushups routinely with a maximal number of about 100 in one hour. The subject topically applied 0.5% (w/v) N—Ac-L-Tyr-L-Tyr-NH2 in WEP442, pH 6.9 solution as prepared in Example 5 to ease the tight muscles on the upper chest about 30 minutes before the exercise. The subject was surprised to find that after the topical application he could now perform pushups with a maximal number of about 200 in one hour without feeling tired. The subject repeated the performance next day with the same enhanced result. To make sure that the enhanced effect on the muscles was not due to the vehicle solution, in the following day the subject topically applied WEP442 solution to the same upper chest about 30 minutes before the exercise. This time the subject could not perform the same number of pushups as before.

The above results show that the bioactive dipeptide derivative of the present invention has the potential of enhancing muscle strength and optimizing exercise performance.

Example 40

A female subject, age 45, having chronic inflammation or eczema with scales, erythema and itch covering large areas of the body for many years, failed to respond by conventional treatments including topical corticosteroids. The subject topically applied twice daily on one set of involved lesions, 0.6% (w/w) N—Ac-L-Tyr-L-Tyr-NHNH2 cream (Example 4) for two weeks. The itch stopped a few minutes after the topical application. At the end of two weeks, the scales and erythema diminished substantially and the treated skin had 75% improvement as judged by clinical evaluation. The subject also topically applied twice daily on another set of involved lesions, 0.7% (w/w) N—Ac-L-Tyr-L-Tyr-NHN-HAc cream (Example 4) for two weeks. The itch stopped immediately after the topical application. At the end of two weeks, the scales and erythema disappeared completely, and the treated skin was smooth and appeared normal. The treated lesions had 100% improvement as judged by clinical evaluation. The results show that the dipeptide derivatives of the present invention have the potential for topical treatment of symptoms or syndromes associated with nerve disorders, disturbed keratinization, inflammation and deranged immune system.

Example 41

A male subject, age 90, had severe arthritis of both knees with edema and pain for many years. The conventional therapy had provided only temporary relief of knee pain and edema. The subject took N—Ac-L-Pro-Gly-NH$_2$ (1 mg) sublingually and kept the dipeptide under the tongue for 15 minutes before swallowing. After a few hours, the edema and pain diminished substantially. The above result shows that the dipeptide derivative of the present invention has the potential of treating inflammation, arthritis, pain, other immune and nerve disorders via systemic administration.

Example 42

A male subject, age 80, had fungal infections of two toe nails for many years. Topical treatments with clotrimazole and salicylic acid with or without glycolic acid had not been successful, as shown by the persistent appearance of white and sandy nail plates. The subject topically applied twice daily to one infected nail plate, 0.5% (w/v) N—Ac-L-Tyr-L-Tyr-NH$_2$ in WEP442, pH 6.7 (Example 5), and to another infected nail plate, 0.5% (w/v) N—Ac-L-Tyr-L-Tyr-NHN-HAc in WEP442, pH 5.5 (Example 5) for several months. After several weeks of topical applications, the white and sandy appearance of both nail plates started to change gradually. Continued topical applications of the formulations should eradicate the nail infections, and the toe nails should start to grow normally. The above result shows that the dipeptide derivatives of the present invention have the potential of treating nail infections and other infections caused by microorganisms.

Example 43

A female subject, age 73, had multiple age spots including lentigines and keratosis on her face. Topical treatments with conventional medications including hydroquinone with or without glycolic acid had been unsuccessful. The subject topically applied twice daily to the left side of her face 1% (w/v) N—Ac-L-Cys-L-Tyr-NH2 in WEP442, pH 6.4 (Example 5), and to the right side of her face 0.4% (w/v) N—Ac-L-Cys-L-Cys-NH2 in WEP442 (Example 5) for several months. After 4 weeks of topical applications, the age spot lesions on both sides of her face started to improve noticeably as shown by the lighter color in appearance. Continued topical applications of the formulations should improve or eradicate lentigines and keratosis of the face. The above result shows that the dipeptide derivatives of the present invention have the potential of treating aging related skin changes including age spots and also for skin lightening.

Example 44

A male subject, age 41, routinely took a shower every morning, then topically applied a conventional antiperspirant product on the underarm skin to prevent perspiration. To test the efficacy of the N-acyldipeptide derivative of the present invention, the subject after the shower, topically applied 0.5% (w/v) N—Ac-L-Tyr-L-Tyr-NH$_2$ in WEP442, pH 6.7 (Example 5) on the left underarm and a control vehicle WEP442 on the right underarm. After two hours, there was profuse sweating in the right underarm as evidenced by the wet shirt in the armpit area. In contrast, there was no sweating in the left underarm as shown by the dry shirt in the armpit area. The left underarm was dry for the next 6-8 hours. The above result shows that N—Ac-Tyr-Tyr-NH$_2$ has the potential for topical application to reduce or prevent perspiration or sweating of underarm, crotch, palm, or other parts of the body.

Example 45

Typical examples of improving eye vision are described as follows.

A male subject, age 41, wore eyeglasses in both eyes for near-sightedness (myopia), and had a routine eye checkup every year. Each time his vision in both eyes got worse, and he required changes in contact lenses in past years. This time, 6 weeks before his checkup, the subject topically applied twice daily 0.5% (w/v) N—Ac-L-Tyr-L-Tyr-NH$_2$ in WEP442, pH 6.7 (Example 5) on the skin around and outside of eye areas and periorbital regions for 6 weeks. During the checkup, the subject and the optometrist were surprised to find that vision in both eyes did not worsen this time, and there was no need to change the prescription for his eyeglasses. The above result shows that N—Ac-Tyr-Tyr-NH$_2$ has the potential for topical application to improve eye vision.

A male subject, age 43, wore contact lenses in both eyes for near-sightedness (myopia), and had a routine eye checkup every year. Each time his vision in both eyes worsened, and he required changes in the prescription for his contact lenses in the past years. This time, one month before his checkup, the subject topically applied once daily 0.5% (w/v) N—Ac-L-Tyr-L-Tyr-NH2 in WEP442, pH 6.7 (Example 5) on the skin around and outside of eye areas and periorbital regions for 4 weeks. During the checkup, the subject and the optometrist were surprised to find that vision in both eyes did not worsen this time, and there was no need to change the prescription for his contact lenses. The above result shows that N—Ac-Tyr-Tyr-NH2 has the potential for topical application to improve eye vision.

Example 46

A typical in vitro screen for anti-tumor or anti-cancer effects was carried out as follows.

An aliquot of 2,000 MB231 breast cancer cells (breast carcinoma cells) in 100 μl DMEM complete media (Sigma Chemical Co.) was plated in a 96 well plate containing at a concentration of 20 μg/ml a test substance or control water. To measure proliferation of the cancer cells, an aliquot of 20 μl of MTS reagent (Promega Co.) was added to each well and the cells were incubated at 370 C for a total of three days. The cells rapidly metabolized MTS reagent and the metabolized MTS reagent was measured at 490 nm at the end of days 1, 2 and 3. The reading was proportional to the number of cancer cells. The decrease in absorbance at each time point indicated fewer cancer cells. At the end of day 3, the decrease in absorbance with respect to the control indicated the inhibition by the test substance. The test showed that N—Ac-L-Val-L-Ala-NH2 had inhibited the growth of breast cancer cells by approximately 12% at the end of 3 days of incubation. The above result shows that N—Ac-L-Val-L-Ala-NH$_2$ has the potential for treatment of breast cancers.

Supplementary Test Results and Summary

In addition to the above Examples, additional test results and summary are described in the following sections.

In one embodiment, a composition for topical application to test its therapeutic effect was formulated by dissolving a bioactive dipeptide derivative of the present invention in a solution prepared from 40 parts water, 40 parts ethanol and 20 parts propylene glycol by volume (WEP442).

In another embodiment, a composition was formulated by dissolving a bioactive dipeptide derivative of the present invention in a non-aqueous solution prepared from 80 parts ethanol and 20 parts propylene glycol by volume (EP82).

In yet another embodiment, a composition was formulated first by dissolving a bioactive dipeptide derivative of the present invention in a solution prepared from 80 parts water and 20 parts propylene glycol by volume (WP82), and the solution thus prepared was mixed with an oil-in-water emulsion or cream.

The concentration of the bioactive ingredient in test solution or cream generally can range from about 0.001% to about 99.9%, with preferred concentration of about 0.01% to 30%, with more preferred concentration of about 0.1% to 10% by weight or by volume (solution composition) of the total composition.

As an illustration, 0.4 g of N—Ac-L-Val-L-Ala-NH2 as a white powder was dissolved in a solution prepared from 40 parts water, 40 parts ethanol and 20 parts propylene glycol by volume (WEP442), and the total volume of the solution was made up to 100 ml. The solution composition thus formulated had pH 5.8 and contained 0.4% N—Ac-L-Val-L-Ala-NH2 in WEP442. Under the same conditions, test solution compositions containing various N-acyldipeptide derivatives of the present invention were prepared in WEP442 with concentrations ranging from 0.1% to 10%.

As an another illustration, 1.0 g of N—Ac-L-Tyr-L-Tyr-NH$_2$ as a white powder was dissolved in a solution prepared from 80 parts ethanol and 20 parts propylene glycol or 80 parts 95% alcohol and 20 parts propylene glycol by volume (WEP4:76:20), and the total volume of the solution was made up to 100 ml. The solution composition thus formulated contained 1% N—Ac-L-Tyr-L-Tyr-NH$_2$ in EP82 or WEP4:76:20 respectively. Under the same conditions, test solution compositions containing various N-acyldipeptide derivatives of the present invention were prepared in EP82 or WEP with concentrations ranging from 0.1% to 10%.

As a further illustration, 0.3 g of N—Ac-L-Val-L-Ala-NH2 as white powder was dissolved in 30 ml warm solution prepared from 80 parts water and 20 parts propylene glycol by volume. The solution thus prepared was mixed with 69.7 g oil-in-water emulsion or cream. The composition thus formulated contained 0.3% N—Ac-L-Val-L-Ala-NH2 in an emulsion or cream composition. Under the same conditions, oil-in-water or cream compositions containing various N-acyldipeptide derivatives of the present invention were formulated with concentrations ranging from 0.1% to 10% by weight of the total composition.

A test composition containing a bioactive dipeptide derivative of the present invention for systemic administration was prepared according to Example 22.

For injection administration, a composition was prepared with or without a thickening agent, such as methyl cellulose. As an illustration, N—Ac-L-Tyr-L-Tyr-NH2, 100 mg, was dissolved in 5 ml water, and the solution was sterilized in an injection vial. The compositions thus prepared contained 2% (w/w) or 20 mg/ml N—Ac-L-Tyr-L-Tyr-NH2 suitable for intra-articular, intra-lesion, or subcutaneous injection, or other systemic administration.

Under the same conditions, the following compositions for systemic administration were prepared: 2% or 20 mg/ml N—Ac-L-Tyr-L-Tyr-NHNH$_2$ in water with or without 1% methyl cellulose; 2% or 20 mg/ml N—Ac-L-Tyr-L-Tyr-NHNHAc in water with or without 1% methyl cellulose; 0.2% or 2 mg/ml N—Ac-L-Val-L-Ala-NH$_2$ in water with or without 1% methyl cellulose; and 0.2% or 2 mg/ml N—Ac-L-Tyr-L-Tyr-OH in water with or without 1% methyl cellulose.

Volunteer Subjects:

In these studies, the participating subjects were as follows:

Subject 1. Male, age 78, had multiple red and itchy inflammation, dermatitis, or eczema lesions, which were resistant to conventional treatments including corticosteroids.
Subject 2. Female, age 31, had small red and itchy lesions which were resistant to topical corticosteroid treatment.
Subject 3. Female, age 43, had multiple red and itchy inflammation, dermatitis, or eczema lesions over the body for many years, which were resistant to conventional treatments including corticosteroids.
Subject 4. Female, age 50, had red and itchy inflammation, dermatitis, or eczema lesions for many years, which were resistant to topical corticosteroid treatment.
Subject 5. Female, age 41, had early stage of aging related skin changes on both forearms as indicated by age spots and wrinkled skin caused by solar damage.
Subject 6. Female, age 52, had age spots, keratoses and wrinkles on both forearms caused by intrinsic and extrinsic aging.
Subject 7. Female, age 51, had age spots, and wrinkles on both forearms caused by intrinsic and extrinsic aging.
Subject 8. Male, age 90, had osteoarthritis of both knees with inflammation and pain for more than 4 years, and had only mild transitory relief from conventional treatments.
Subject 9. Female, age 41, had sensitive skin with inflammatory lesions on the body.
Subject 10. Male, age 42, had mosquito bites and inflammatory lesions on the body.
Subject 11. Male, age 41, had stretch marks all over the body due to massive weight loss.
Subject 12. Male, age 41, had dermatitis and inflammatory lesions on the left palm.
Subject 13. Female, age 52, had chigger bites with multiple lesions on her legs.
Subject 14. Female, age 73, had multiple age spots including lentigines and keratosis on her face.

Other subjects with various skin and medical conditions and disorders also participated in the present tests and studies.

Test Methods.

In one embodiment, the test compositions containing N-acyldipeptide derivatives of the present invention were tested in an in vitro screen for their biological efficacy in cell cultures as described in Examples 21 and 46.

In another embodiment, the volunteer subject topically applied the test compositions containing N-acyldipeptide derivatives of the present invention on involved skin or lesions once or twice daily for several weeks or until the involved lesions completely cleared and clinically changed to normal skin. As a control study, the subject also topically applied a vehicle control composition on the involved skin or lesions twice daily for the same period.

In yet another embodiment, the volunteer subject topically applied once or twice daily the test compositions containing N-acyldipeptide derivatives of the present invention on the skin site above arthritic joints or painful muscles to provide therapeutic effects for the systemic disorders via topical administration.

In yet another embodiment, the volunteer subject injected intra-articularly into a knee joint a test composition containing a bioactive dipeptide derivative of the present invention to improve and reduce arthritic inflammation and pain of the joint.

Some test results are summarized as follows.
DK: Disturbed keratinization
AG: Aging related changes of skin, nail and hair
DI: Deranged immune disorders and inflammation
ND: Nerve disorders
1+: 25% Efficacy 2+: 50% Efficacy 3+: 75% Efficacy 4+: 95-100% Efficacy

| Ala Peptide Derivative | DK | AG | DI | ND | |
|---|---|---|---|---|---|
| N-Ac-L-Ile-L-Ala-NH$_2$ | 2+ | 2+ | 4+ | 4+ | |
| N-Ac-L-Ile-L-Ala-OH | 2+ | 2+ | 2+ | 2+ | |
| N-Ac-L-Leu-L-Ala-NH$_2$ | 3+ | 3+ | 4+ | 4+ | |
| N-Ac-L-Leu-L-Ala-OH | 2+ | 2+ | 3+ | 3+ | |
| N-Ac-L-Val-L-Ala-NH$_2$ | 4+ | 4+ | 4+ | 4+ | also for joints, muscles, breast cancer |
| N-Ac-L-Val-L-Ala-OH | 2+ | 2+ | 3+ | 4+ | |
| N-Pr-L-Val-L-Ala-OH | 2+ | 2+ | 3+ | 4+ | |
| N-Ac-L-Cys-L-Cys-NH$_2$ | 2+ | 3+ | 2+ | 2+ | also for age spots |
| N-Ac-L-Cys-L-Cys-OH | 2+ | 3+ | 2+ | 2+ | also for age spots |
| N-Ac-β-Ala-Gly-NH$_2$ | 2+ | 2+ | 2+ | 2+ | |
| N-Ac-L-Asn-Gly-NH$_2$ | 2+ | 2+ | 2+ | 2+ | |
| N-Ac-Abz-Gly-NH$_2$ | 2+ | 2+ | 3+ | 3+ | |
| N-Ac-L-Cys-Gly-NH$_2$ | 2+ | 2+ | 2+ | 2+ | |
| N-Ac-Gaba-Gly-NH$_2$ | 2+ | 2+ | 2+ | 2+ | |
| N-Ac-Gly-Gly-NH$_2$ | 2+ | 2+ | 2+ | 2+ | |
| N-Ac-L-Gln-Gly-NH$_2$ | 2+ | 2+ | 2+ | 2+ | |
| N-Ac-L-His-Gly-NH$_2$ | 2+ | 2+ | 2+ | 2+ | |
| N-Ac-L-Ile-Gly-NH$_2$ | 3+ | 3+ | 4+ | 4+ | |
| N-Ac-L-Ile-Gly-OH | 2+ | 2+ | 3+ | 4+ | |
| N-Ac-L-Leu-Gly-NH$_2$ | 3+ | 3+ | 4+ | 4+ | |
| N-Ac-L-Leu-Gly-OH | 2+ | 2+ | 3+ | 3+ | |
| N-Pr-L-Leu-Gly-OH | 2+ | 2+ | 3+ | 3+ | |
| N-Ac-L-Pro-Gly-NH$_2$ | 2+ | 2+ | 3+ | 4+ | |
| N-Ac-L-Ser-Gly-NH$_2$ | 2+ | 2+ | 2+ | 2+ | |
| N-Ac-L-Tyr-Gly-NH$_2$ | 2+ | 2+ | 2+ | 2+ | |
| N-Z-L-Tyr-Gly-NH$_2$ | 2+ | 2+ | 2+ | 2+ | |
| N-Ac-L-Val-Gly-NH$_2$ | 2+ | 2+ | 4+ | 4+ | |
| N-Ac-L-Val-Gly-OH | 2+ | 2+ | 3+ | 4+ | |
| N-Ac-βAla-L-His-NH$_2$ | 2+ | 2+ | 2+ | 2+ | |
| N,N'-diAc-βAla-L-His-NH$_2$ | 2+ | 2+ | 2+ | 2+ | |
| N-Ac-L-Ala-L-Ile-NH$_2$ | 2+ | 2+ | 3+ | 3+ | |
| N-Ac-L-Ile-L-Ile-NH$_2$ | 3+ | 3+ | 4+ | 4+ | |
| N-Ac-L-Leu-L-Leu-NH$_2$ | 2+ | 2+ | 2+ | 2+ | |
| N-Ac-Gly-L-Pro-NH$_2$ | 2+ | 2+ | 2+ | 2+ | |
| N-Ac-L-Cys-L-Tyr-NH$_2$ | 2+ | 2+ | 2+ | 3+ | |
| N-Ac-L-Ile-L-Tyr-NH$_2$ | 2+ | 2+ | 2+ | 2+ | |
| N-Ac-L-Leu-L-Tyr-NH$_2$ | 2+ | 2+ | 2+ | 2+ | |
| N-Ac-L-Tyr-L-Tyr-NH$_2$ | 4+ | 4+ | 4+ | 4+ | also for joints, muscles, infections |
| N-Ac-L-Val-L-Tyr-NH$_2$ | 2+ | 2+ | 2+ | 2+ | |
| N-Ac-L-Tyr-L-Tyr-OH | 3+ | 4+ | 3+ | 4+ | |

-continued

| Ala Peptide Derivative | DK | AG | DI | ND | |
|---|---|---|---|---|---|
| N-Ac-L-Tyr-L-Tyr-OEt | 2+ | 2+ | 2+ | 2+ | |
| N-Ac-L-Tyr-L-Tyr-NHNH$_2$ | 3+ | 3+ | 2+ | 2+ | |
| N-Ac-L-Tyr-L-Tyr-NHNHAc | 4+ | 3+ | 4+ | 4+ | also for infections |
| N-Ac-L-Tyr-L-Hpg-NH$_2$ | 2+ | 2+ | 2+ | 2+ | |
| N-Ac-L-Phe-L-Phe-NH$_2$ | 2+ | 2+ | 2+ | 2+ | |
| N-Ac-L-Trp-L-Trp-NH$_2$ | 2+ | 2+ | 2+ | 2+ | |

The bioactive dipeptide derivatives of the present invention can be topically administered to provide topical effects or to exert therapeutic effects for systemic diseases. As shown in Examples 27, 31, 32, 39, 44 and 45, the compositions containing N-acyldipeptide derivatives have the potential to improve arthritis and pain of joints, enhance muscle strength, improve eye vision and to reduce or prevent sweating or perspiration of underarm, crotch, palm, or other parts of the body, via topical application. The bioactive dipeptide derivatives of the present invention can also be given by systemic administration to improve systemic diseases. As shown in the Example 23, the composition containing the bioactive dipeptide derivative has the potential to improve arthritis of knee joints via intra-articular injection.

The increased skin thickness or plump as shown in the Examples was not due to increased water retention or edema of the skin because the thickness maintained for many months after discontinuation of the treatment. As shown earlier, the skin biopsies from the plump skin show increased biosynthesis of GAGs, collagen fibers and elastic fibers, and less clumping of melanin as evidenced by histochemical analysis. Therefore, when a substance is found to plump or increase the skin thickness, the substance is reasonably expected or predicted to improve aging related skin changes including fine lines, wrinkles, photoaging, age spots, blotches, hyperpigmented skin, mottled skin, and for younger-looking skin and skin lightening.

Therefore, while not wishing to be bound by theory, it is believed that a composition of the present invention has the potential for topical treatment of aging related skin changes including wrinkles and older-looking skin, because a bioactive dipeptide derivative can increase the skin thickness or plump the skin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating skin, comprising topically administering to skin in need of increased thickness or treatment for abnormal or diminished synthesis of collagen, glycosaminoglycans, proteoglycans, or elastin a composition comprising a therapeutically effective amount of a dipeptide derivative of formula (I):

R$_1$-AAB-AAC-R$_2$     Formula (I)

or an isomer or salt thereof, and optionally a pharmaceutically or cosmetically acceptable carrier, wherein R$_1$ is an acyl radical having up to 19 carbon atoms; AAB is Tyr and AAC is Tyr, or AAB is Val and AAC is Ala; R$_2$ is OR$_3$, NHR$_4$, or NHNHR$_5$; R$_3$ is H, an alkyl, aralkyl, or aryl radical having up to 19 carbon atoms; and R$_4$ or R$_5$ is independently H, OH, an alkyl, aralkyl, or aryl radical having up to 19 carbon atoms, thereby increasing skin thickness or treating abnormal or diminished synthesis of collagen, glycosaminoglycans, proteoglycans, or elastin.

2. The method of claim 1, wherein AAB is Tyr and AAC is Tyr.

3. The method of claim 1, wherein AAB is Val and AAC is Ala.

4. The method of claim 1, wherein the dipeptide derivative is selected from the group consisting of N—Ac-Tyr-Tyr-NH2, N—Ac-Tyr-Tyr-OH, N—Ac-Tyr-Tyr-OEt, N—Ac-Tyr-Tyr-NHNH$_2$, N—Ac-Tyr-Tyr-NHNHAc, N—Ac-Tyr-Tyr-NHOH, N—Pr-Tyr-Tyr-NH$_2$, N—Pr-Tyr-Tyr-OH, N—Pr-Tyr-Tyr-OEt, N—Pr-Tyr-Tyr-NHNH$_2$, and N—Pr-Tyr-Tyr-NHNHPr.

5. The method of claim 1, wherein the dipeptide derivative is selected from the group consisting of N—Ac-Val-Ala-NH2, N—Ac—Val-Ala-OH, N—Ac—Val-Ala-NHOH, N—Pr—Val-Ala-NH2, and N—Pr-Val-Ala-OH.

6. The method of claim 1, wherein the dipeptide derivative is selected from the group consisting of N—Ac-Tyr-Tyr-NH$_2$ and N—Ac-Val-Ala-NH$_2$.

7. The method of claim 1, being a method of treating skin in need of increased skin thickness.

8. The method of claim 1, being a method of treating skin in need of treatment for abnormal or diminished synthesis of collagen, glycosaminoglycans, proteoglycans, or elastin.

9. The method of claim 8, being a method of treating skin in need of treatment for abnormal or diminished synthesis of elastin.

10. A method of increasing skin thickness in a subject in need thereof, comprising topically administering to the skin of the subject a therapeutically effective amount of a dipeptide derivative of formula (I):

  Formula (I)

or an isomer or salt thereof, and optionally a pharmaceutically or cosmetically acceptable carrier, wherein $R_1$ is an acyl radical having up to 19 carbon atoms; AAB is Tyr and AAC is Tyr, or AAB is Val and AAC is Ala; $R_2$ is $OR_3$, $NHR_4$, or $NHNHR_5$; $R_3$ is H, an alkyl, aralkyl, or aryl radical having up to 19 carbon atoms; and $R_4$ or $R_5$ is independently H, OH, an alkyl, aralkyl, or aryl radical having up to 19 carbon atoms.

11. The method of claim 10, wherein AAB is Tyr and AAC is Tyr.

12. The method of claim 10, wherein AAB is Val and AAC is Ala.

13. The method of claim 10, wherein the dipeptide derivative is selected from the group consisting of N—Ac-Tyr-Tyr-NH2, N—Ac-Tyr-Tyr-OH, N—Ac-Tyr-Tyr-OEt, N—Ac-Tyr-Tyr-NHNH$_2$, N—Ac-Tyr-Tyr-NHNHAc, N—Ac-Tyr-Tyr-NHOH, N—Pr-Tyr-Tyr-NH$_2$, N—Pr-Tyr-Tyr-OH, N—Pr-Tyr-Tyr-OEt, N—Pr-Tyr-Tyr-NHNH$_2$, and N—Pr-Tyr-Tyr-NHNHPr.

14. The method of claim 10, wherein the dipeptide derivative is selected from the group consisting of N—Ac-Val-Ala-NH2, N—Ac—Val-Ala-OH, N—Ac—Val-Ala-NHOH, N—Pr—Val-Ala-NH2, and N—Pr-Val-Ala-OH.

15. The method of claim 10, wherein the dipeptide derivative is selected from the group consisting of N—Ac-Tyr-Tyr-NH2 and N—Ac-Val-Ala-NH2.

16. A method of reducing wrinkles in a subject in need thereof, comprising topically administering to the skin of the subject a therapeutically effective amount of a dipeptide derivative of formula (I):

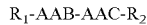  Formula (I)

or an isomer or salt thereof, and optionally a pharmaceutically or cosmetically acceptable carrier, wherein $R_1$ is an acyl radical having up to 19 carbon atoms; AAB is Tyr and AAC is Tyr, or AAB is Val and AAC is Ala; $R_2$ is $OR_3$, $NHR_4$, or $NHNHR_5$; $R_3$ is H, an alkyl, aralkyl, or aryl radical having up to 19 carbon atoms; and $R_4$ or $R_5$ is independently H, OH, an alkyl, aralkyl, or aryl radical having up to 19 carbon atoms.

17. The method of claim 16, wherein AAB is Tyr and AAC is Tyr.

18. The method of claim 16, wherein AAB is Val and AAC is Ala.

19. The method of claim 16, wherein the dipeptide derivative is selected from the group consisting of N—Ac-Tyr-Tyr-NH2, N—Ac-Tyr-Tyr-OH, N—Ac-Tyr-Tyr-OEt, N—Ac-Tyr-Tyr-NHNH$_2$, N—Ac-Tyr-Tyr-NHNHAc, N—Ac-Tyr-Tyr-NHOH, N—Pr-Tyr-Tyr-NH$_2$, N—Pr-Tyr-Tyr-OH, N—Pr-Tyr-Tyr-OEt, N—Pr-Tyr-Tyr-NHNH$_2$, and N—Pr-Tyr-Tyr-NHNHPr.

20. The method of claim 16, wherein the dipeptide derivative is selected from the group consisting of N—Ac-Val-Ala-NH2, N—Ac—Val-Ala-OH, N—Ac—Val-Ala-NHOH, N—Pr—Val-Ala-NH2, and N—Pr-Val-Ala-OH.

21. The method of claim 16, wherein the dipeptide derivative is selected from the group consisting of N—Ac-Tyr-Tyr-NH$_2$ and N—Ac-Val-Ala-NH$_2$.

* * * * *